(12) United States Patent
Beira et al.

(10) Patent No.: US 12,402,960 B2
(45) Date of Patent: Sep. 2, 2025

(54) MECHANICAL MANIPULATOR FOR SURGICAL INSTRUMENTS

(71) Applicant: Ecole Polytechnique Federale De Lausanne (EPFL), Lausanne (CH)

(72) Inventors: Ricardo Daniel Rita Beira, Lausanne (CH); Reymond Clavel, Oulens-sous-Echallens (CH); Hannes Bleuler, Buchillon (CH)

(73) Assignee: Ecole Polytechnique Federale De Lausanne (EPFL), Lausanne (CH)

( * ) Notice: Subject to any disclaimer, the term of this patent is extended or adjusted under 35 U.S.C. 154(b) by 737 days.

(21) Appl. No.: 17/385,824

(22) Filed: Jul. 26, 2021

(65) Prior Publication Data

US 2021/0369360 A1    Dec. 2, 2021

Related U.S. Application Data

(63) Continuation-in-part of application No. 16/701,063, filed on Dec. 2, 2019, now Pat. No. 11,200,980,
(Continued)

(30) Foreign Application Priority Data

Oct. 11, 2010   (EP) .................................... 10187088
Oct. 11, 2010   (EP) .................................... 10187097
May 18, 2012   (CH) .................................... 00702/12

(51) Int. Cl.
*A61B 34/30*    (2016.01)
*A61B 17/29*    (2006.01)
(Continued)

(52) U.S. Cl.
CPC .............. *A61B 34/30* (2016.02); *A61B 34/71* (2016.02); *F16H 19/08* (2013.01);
(Continued)

(58) Field of Classification Search
CPC . A61B 34/30; A61B 34/71; A61B 2017/2906; A61B 2090/371; F16H 19/08; Y10T 74/18848
See application file for complete search history.

(56) References Cited

U.S. PATENT DOCUMENTS 2,764,301 A    9/1956  Goertz et al.
2,771,199 A   11/1956  Jelatis
(Continued)

FOREIGN PATENT DOCUMENTS

CN    101027010 A    8/2007
CN    101584594 A   11/2009
(Continued)

OTHER PUBLICATIONS

US 9,232,978 B2, 01/2016, Shellenberger et al. (withdrawn)
(Continued)

*Primary Examiner* — Ziaul Karim
(74) *Attorney, Agent, or Firm* — Cooley LLP

(57) ABSTRACT

A novel mechanical system, based on a new cable driven mechanical transmission, able to provide sufficient dexterity, stiffness, speed, precision and payload capacity to actuate multi-DOF micro-manipulators. Besides the possibility of being used in several articulated surgical instruments and robotic systems for surgery or other applications involving remote manipulation, it enables the design of a novel fully mechanical surgical instrument, which offer the advantages of: conventional laparoscopy (low cost, tactile feedback, high payload capacity) combined with the advantages of single port surgery (single incision, starless surgery, navigation through several quadrants of the abdominal cavity) and robotic surgery (greater degrees of freedom, short learning curve, high stiffness, high precision, increased intuition). The unique design of the proposed system provides an intuitive user interface to achieve such enhanced
(Continued)

manoeuvrability, allowing each Joint of a teleoperated slave system to be driven by controlling the position of a mechanically connected master unit.

15 Claims, 17 Drawing Sheets

Related U.S. Application Data which is a continuation of application No. 16/442,435, filed on Jun. 14, 2019, now Pat. No. 10,510,447, application No. 17/385,824 is a continuation of application No. 16/153,695, filed on Oct. 5, 2018, now Pat. No. 11,076,922, said application No. 16/442,435 is a continuation of application No. 15/633,611, filed on Jun. 26, 2017, now Pat. No. 10,325,072, which is a continuation of application No. 14/233,184, filed as application No. PCT/IB2012/053786 on Jul. 25, 2012, now Pat. No. 9,696,700, said application No. 16/153,695 is a continuation of application No. 13/878,924, filed as application No. PCT/IB2011/054476 on Oct. 11, 2011, now Pat. No. 10,092,359.

(60) Provisional application No. 61/511,994, filed on Jul. 27, 2011.

(51) Int. Cl.
*A61B 34/00* (2016.01)
*A61B 90/00* (2016.01)
*F16H 19/08* (2006.01)

(52) U.S. Cl.
CPC . *A61B 2017/2906* (2013.01); *A61B 2090/371* (2016.02); *Y10T 74/18848* (2015.01)

(56) References Cited

U.S. PATENT DOCUMENTS

| | | | |
|---|---|---|---|
| 2,774,488 A | 12/1956 | Goertz et al. | |
| 2,846,084 A | 8/1958 | Goertz et al. | |
| 3,065,863 A | 11/1962 | Saunders, Jr. et al. | |
| 3,095,096 A | 6/1963 | Chesley | |
| 3,212,651 A | 10/1965 | Specht et al. | |
| 3,261,480 A | 7/1966 | Haaker et al. | |
| 3,280,991 A | 10/1966 | Melton et al. | |
| 3,297,172 A | 1/1967 | Haaker et al. | |
| 3,391,801 A | 7/1968 | Haaker | |
| 3,425,569 A | 2/1969 | Haaker et al. | |
| 3,683,747 A | 8/1972 | Pettit | |
| 4,221,516 A | 9/1980 | Haaker et al. | |
| 4,522,196 A | 6/1985 | Cunningham et al. | |
| 4,756,655 A | 7/1988 | Jameson | |
| 5,147,357 A | 9/1992 | Rose et al. | |
| 5,176,352 A | 1/1993 | Braun | |
| 5,184,601 A | 2/1993 | Putman | |
| 5,207,114 A * | 5/1993 | Salisbury, Jr. | F16H 19/005 74/89.22 |
| 5,209,747 A | 5/1993 | Knoepfler | |
| 5,279,309 A | 1/1994 | Taylor et al. | |
| 5,304,203 A | 4/1994 | El-Mallawany et al. | |
| 5,308,358 A | 5/1994 | Bond et al. | |
| 5,330,502 A | 7/1994 | Hassler et al. | |
| 5,368,606 A | 11/1994 | Marlow et al. | |
| 5,382,885 A | 1/1995 | Salcudean et al. | |
| 5,383,888 A | 1/1995 | Zvenyatsky et al. | |
| 5,484,435 A | 1/1996 | Fleenor et al. | |
| 5,591,119 A | 1/1997 | Adair | |
| 5,599,151 A | 2/1997 | Daum et al. | |
| 5,603,723 A | 2/1997 | Aranyi et al. | |
| 5,631,973 A | 5/1997 | Green | |
| 5,649,955 A | 7/1997 | Hashimoto et al. | |
| 5,649,956 A | 7/1997 | Jensen et al. | |
| 5,657,429 A | 8/1997 | Wang et al. | |
| 5,710,870 A * | 1/1998 | Ohm | B25J 19/02 700/262 |
| 5,716,352 A | 2/1998 | Viola et al. | |
| 5,735,874 A | 4/1998 | Measamer et al. | |
| 5,745,387 A | 4/1998 | Corby, Jr. et al. | |
| 5,779,727 A | 7/1998 | Orejola | |
| 5,784,542 A * | 7/1998 | Ohm | A61B 34/35 901/34 |
| 5,792,045 A | 8/1998 | Adair | |
| 5,797,900 A | 8/1998 | Madhani et al. | |
| 5,810,716 A | 9/1998 | Mukherjee et al. | |
| 5,810,805 A | 9/1998 | Sutcu et al. | |
| 5,828,813 A | 10/1998 | Ohm | |
| 5,876,325 A | 3/1999 | Mizuno et al. | |
| 5,908,436 A | 6/1999 | Cuschieri et al. | |
| 5,931,832 A | 8/1999 | Jensen | |
| 5,951,587 A | 9/1999 | Qureshi et al. | |
| 5,976,122 A | 11/1999 | Madhani et al. | |
| 6,026,701 A | 2/2000 | Reboulet | |
| 6,063,095 A | 5/2000 | Wang et al. | |
| 6,120,433 A | 9/2000 | Mizuno et al. | |
| 6,132,368 A | 10/2000 | Cooper | |
| 6,197,017 B1 | 3/2001 | Brock et al. | |
| 6,206,903 B1 | 3/2001 | Ramans | |
| 6,233,504 B1 | 5/2001 | Das et al. | |
| 6,281,651 B1 | 8/2001 | Haanpaa et al. | |
| 6,312,435 B1 | 11/2001 | Wallace et al. | |
| 6,331,181 B1 | 12/2001 | Tierney et al. | |
| 6,358,249 B1 | 3/2002 | Chen et al. | |
| 6,361,534 B1 | 3/2002 | Chen et al. | |
| 6,364,879 B1 | 4/2002 | Chen et al. | |
| 6,371,952 B1 | 4/2002 | Madhani et al. | |
| 6,375,610 B2 | 4/2002 | Verschuur | |
| 6,394,998 B1 | 5/2002 | Wallace et al. | |
| 6,435,794 B1 | 8/2002 | Springer | |
| 6,436,107 B1 | 8/2002 | Wang et al. | |
| 6,459,926 B1 | 10/2002 | Nowlin et al. | |
| 6,491,701 B2 | 12/2002 | Tierney et al. | |
| 6,554,844 B2 | 4/2003 | Lee et al. | |
| 6,587,750 B2 | 7/2003 | Gerbi et al. | |
| 6,594,552 B1 | 7/2003 | Nowlin et al. | |
| 6,671,581 B2 | 12/2003 | Niemeyer et al. | |
| 6,699,177 B1 | 3/2004 | Wang et al. | |
| 6,723,106 B1 | 4/2004 | Charles et al. | |
| 6,786,896 B1 | 9/2004 | Madhani et al. | |
| 6,788,999 B2 | 9/2004 | Green | |
| 6,799,065 B1 | 9/2004 | Niemeyer | |
| 6,840,938 B1 | 1/2005 | Morley et al. | |
| 6,850,817 B1 | 2/2005 | Green | |
| 6,852,107 B2 | 2/2005 | Wang et al. | |
| 6,879,880 B2 | 4/2005 | Nowlin et al. | |
| 6,902,560 B1 | 6/2005 | Morley et al. | |
| 6,913,613 B2 | 7/2005 | Schwarz et al. | |
| 6,951,535 B2 | 10/2005 | Ghodoussi et al. | |
| 6,991,627 B2 | 1/2006 | Madhani et al. | |
| 6,994,708 B2 | 2/2006 | Manzo | |
| 7,025,064 B2 | 4/2006 | Wang et al. | |
| 7,048,745 B2 | 5/2006 | Tierney et al. | |
| 7,083,571 B2 | 8/2006 | Wang et al. | |
| 7,090,637 B2 | 8/2006 | Danitz et al. | |
| 7,101,363 B2 | 9/2006 | Nishizawa et al. | |
| 7,122,032 B2 | 10/2006 | Shinmura et al. | |
| 7,204,836 B2 | 4/2007 | Wagner et al. | |
| 7,232,440 B2 | 6/2007 | Dumbauld et al. | |
| 7,241,289 B2 | 7/2007 | Braun | |
| 7,306,597 B2 | 12/2007 | Manzo | |
| 7,316,681 B2 | 1/2008 | Madhani et al. | |
| 7,331,967 B2 | 2/2008 | Lee et al. | |
| 7,338,513 B2 | 3/2008 | Lee et al. | |
| 7,364,582 B2 | 4/2008 | Lee | |
| 7,373,219 B2 | 5/2008 | Nowlin et al. | |
| 7,379,790 B2 | 5/2008 | Toth et al. | |
| 7,398,707 B2 | 7/2008 | Morley et al. | |
| 7,481,824 B2 | 1/2009 | Boudreaux et al. | |
| 7,549,998 B2 | 6/2009 | Braun | |
| 7,594,912 B2 | 9/2009 | Cooper et al. | |
| 7,608,039 B1 | 10/2009 | Todd | |
| 7,615,002 B2 | 11/2009 | Rothweiler et al. | |

(56) References Cited

U.S. PATENT DOCUMENTS

| | | |
|---|---|---|
| 7,615,067 B2 | 11/2009 | Lee et al. |
| 7,674,255 B2 | 3/2010 | Braun |
| 7,699,855 B2 | 4/2010 | Anderson et al. |
| 7,744,608 B2 * | 6/2010 | Lee ............ A61B 34/20 606/1 |
| 7,756,036 B2 | 7/2010 | Druke et al. |
| 7,819,894 B2 | 10/2010 | Mitsuishi et al. |
| 7,824,401 B2 | 11/2010 | Manzo et al. |
| 7,828,798 B2 | 11/2010 | Buysse et al. |
| 7,833,156 B2 | 11/2010 | Williams et al. |
| 7,865,266 B2 | 1/2011 | Moll et al. |
| 7,890,211 B2 | 2/2011 | Green |
| 7,914,521 B2 | 3/2011 | Wang et al. |
| 7,935,130 B2 | 5/2011 | Williams |
| 7,976,458 B2 | 7/2011 | Stefanchik et al. |
| 8,004,229 B2 | 8/2011 | Nowlin et al. |
| 8,048,084 B2 | 11/2011 | Schneid |
| 8,100,133 B2 | 1/2012 | Mintz et al. |
| 8,105,320 B2 | 1/2012 | Manzo |
| 8,114,017 B2 | 2/2012 | Bacher |
| 8,137,263 B2 | 3/2012 | Marescaux et al. |
| 8,142,447 B2 | 3/2012 | Cooper et al. |
| 8,224,485 B2 | 7/2012 | Unsworth |
| 8,246,617 B2 | 8/2012 | Welt et al. |
| 8,267,958 B2 | 9/2012 | Braun |
| 8,287,469 B2 | 10/2012 | Stefanchik et al. |
| 8,292,889 B2 | 10/2012 | Cunningham et al. |
| 8,306,656 B1 | 11/2012 | Schaible et al. |
| 8,308,738 B2 | 11/2012 | Nobis et al. |
| 8,332,072 B1 | 12/2012 | Schaible et al. |
| 8,336,751 B2 | 12/2012 | Scirica |
| 8,347,754 B1 | 1/2013 | Veltri et al. |
| 8,353,898 B2 | 1/2013 | Lutze et al. |
| 8,357,161 B2 | 1/2013 | Mueller |
| 8,382,742 B2 | 2/2013 | Hermann et al. |
| 8,388,516 B2 | 3/2013 | Sholev |
| 8,403,832 B2 | 3/2013 | Cunningham et al. |
| 8,414,475 B2 | 4/2013 | Sholev |
| 8,418,904 B2 | 4/2013 | Wenchell et al. |
| 8,419,717 B2 | 4/2013 | Diolaiti et al. |
| 8,423,186 B2 | 4/2013 | Itkowitz et al. |
| 8,433,389 B2 | 4/2013 | Geiger et al. |
| 8,435,171 B2 | 5/2013 | Sholev |
| 8,496,152 B2 | 7/2013 | Viola |
| 8,518,024 B2 | 8/2013 | Williams et al. |
| 8,523,900 B2 | 9/2013 | Jinno et al. |
| 8,527,094 B2 | 9/2013 | Kumar et al. |
| 8,540,748 B2 | 9/2013 | Murphy et al. |
| 8,562,592 B2 | 10/2013 | Conlon et al. |
| 8,568,444 B2 | 10/2013 | Cunningham |
| 8,579,176 B2 | 11/2013 | Smith et al. |
| 8,591,397 B2 | 11/2013 | Berkelman et al. |
| 8,597,280 B2 | 12/2013 | Cooper et al. |
| 8,602,287 B2 | 12/2013 | Yates et al. |
| 8,603,077 B2 | 12/2013 | Cooper et al. |
| 8,616,431 B2 | 12/2013 | Timm et al. |
| 8,617,203 B2 | 12/2013 | Stefanchik et al. |
| 8,644,988 B2 | 2/2014 | Prisco et al. |
| 8,663,270 B2 | 3/2014 | Donnigan et al. |
| 8,668,689 B2 | 3/2014 | Dumbauld et al. |
| 8,668,702 B2 | 3/2014 | Awtar et al. |
| 8,690,755 B2 | 4/2014 | Sholev |
| 8,696,666 B2 | 4/2014 | Sanai et al. |
| 8,709,000 B2 | 4/2014 | Madhani et al. |
| 8,761,930 B2 | 6/2014 | Nixon |
| 8,768,509 B2 | 7/2014 | Unsworth |
| 8,792,688 B2 | 7/2014 | Unsworth |
| 8,801,752 B2 | 8/2014 | Fortier et al. |
| 8,816,628 B2 | 8/2014 | Nowlin et al. |
| 8,818,560 B2 | 8/2014 | Kishi |
| 8,821,480 B2 | 9/2014 | Burbank |
| 8,827,135 B2 | 9/2014 | Amid et al. |
| 8,828,046 B2 | 9/2014 | Stefanchik et al. |
| 8,845,517 B2 | 9/2014 | Russo |
| 8,845,622 B2 | 9/2014 | Paik et al. |
| 8,862,268 B2 | 10/2014 | Robinson et al. |
| 8,870,049 B2 | 10/2014 | Amid et al. |
| 8,870,867 B2 | 10/2014 | Walberg et al. |
| 8,887,979 B2 | 11/2014 | Mastri et al. |
| 8,894,674 B2 | 11/2014 | Balanev et al. |
| 8,919,348 B2 | 12/2014 | Williams et al. |
| 8,930,027 B2 | 1/2015 | Schaible et al. |
| 8,945,098 B2 | 2/2015 | Seibold et al. |
| 8,961,499 B2 | 2/2015 | Paik et al. |
| 8,961,514 B2 | 2/2015 | Garrison |
| 8,968,187 B2 | 3/2015 | Kleyman et al. |
| 8,989,844 B2 | 3/2015 | Cinquin et al. |
| 8,992,564 B2 | 3/2015 | Jaspers |
| 9,023,015 B2 | 5/2015 | Penna |
| 9,033,998 B1 | 5/2015 | Schaible et al. |
| 9,044,238 B2 | 6/2015 | Orszulak |
| 9,084,606 B2 | 7/2015 | Greep |
| 9,113,860 B2 | 8/2015 | Viola et al. |
| 9,113,861 B2 | 8/2015 | Martin et al. |
| 9,149,339 B2 | 10/2015 | Unsworth |
| 9,204,939 B2 | 12/2015 | Frimer et al. |
| 9,216,013 B2 | 12/2015 | Scirica et al. |
| 9,295,379 B2 | 3/2016 | Sholev |
| 9,307,894 B2 | 4/2016 | Von Grunberg et al. |
| 9,333,040 B2 | 5/2016 | Shellenberger et al. |
| 9,345,545 B2 | 5/2016 | Shellenberger et al. |
| 9,360,934 B2 | 6/2016 | Ruiz Morales et al. |
| 9,421,003 B2 | 8/2016 | Williams et al. |
| 9,474,580 B2 | 10/2016 | Hannaford et al. |
| 9,480,531 B2 | 11/2016 | Von Grunberg |
| 9,492,240 B2 | 11/2016 | Itkowitz et al. |
| 9,504,456 B2 | 11/2016 | Frimer et al. |
| 9,504,527 B2 | 11/2016 | Smaby et al. |
| 9,554,794 B2 | 1/2017 | Baber et al. |
| 9,603,672 B2 | 3/2017 | Shellenberger et al. |
| 9,669,542 B2 | 6/2017 | Karguth et al. |
| 9,696,700 B2 | 7/2017 | Beira et al. |
| 9,757,204 B2 | 9/2017 | Frimer et al. |
| 9,757,206 B2 | 9/2017 | Frimer et al. |
| 9,763,741 B2 | 9/2017 | Alvarez et al. |
| 9,782,230 B2 | 10/2017 | Smaby et al. |
| 9,795,282 B2 | 10/2017 | Sholev et al. |
| 9,795,454 B2 | 10/2017 | Seeber et al. |
| 9,825,455 B2 | 11/2017 | Sandhu et al. |
| 9,872,737 B2 | 1/2018 | Nixon |
| 9,877,794 B2 | 1/2018 | Csiky |
| D816,243 S | 4/2018 | Barber |
| 9,937,013 B2 | 4/2018 | Frimer et al. |
| 9,943,372 B2 | 4/2018 | Sholev et al. |
| 10,028,792 B2 | 7/2018 | Frimer et al. |
| 10,039,609 B2 | 8/2018 | Frimer et al. |
| 10,039,820 B2 | 8/2018 | Coller et al. |
| 10,052,157 B2 | 8/2018 | Frimer et al. |
| 10,064,691 B2 | 9/2018 | Frimer et al. |
| 10,071,488 B2 | 9/2018 | Robinson et al. |
| 10,092,164 B2 | 10/2018 | Sholev et al. |
| 10,092,359 B2 | 10/2018 | Beira et al. |
| 10,092,365 B2 | 10/2018 | Seeber |
| 10,123,844 B2 | 11/2018 | Nowlin et al. |
| 10,136,956 B2 | 11/2018 | Seeber |
| 10,188,471 B2 | 1/2019 | Brisson |
| 10,201,392 B2 | 2/2019 | Frimer et al. |
| 10,265,129 B2 | 4/2019 | Beira |
| 10,325,072 B2 | 6/2019 | Beira et al. |
| 10,357,320 B2 | 7/2019 | Beira |
| 10,357,324 B2 | 7/2019 | Flatt et al. |
| 10,363,055 B2 | 7/2019 | Beira et al. |
| 10,413,374 B2 | 9/2019 | Chassot et al. |
| 10,510,447 B2 | 12/2019 | Beira et al. |
| 10,548,680 B2 | 2/2020 | Beira |
| 10,568,709 B2 | 2/2020 | Beira |
| 10,603,123 B2 | 3/2020 | Vakharia et al. |
| 10,646,291 B2 | 5/2020 | Turner |
| 10,646,294 B2 | 5/2020 | Beira |
| 10,786,272 B2 | 9/2020 | Beira |
| 10,792,113 B2 | 10/2020 | Cuthbertson et al. |
| 10,864,049 B2 | 12/2020 | Beira |
| 10,864,052 B2 | 12/2020 | Beira |
| 11,039,820 B2 | 6/2021 | Beira |

(56) References Cited

U.S. PATENT DOCUMENTS

| | | |
|---|---|---|
| 11,058,503 B2 | 7/2021 | Chassot et al. |
| 11,076,922 B2 | 8/2021 | Beira et al. |
| 11,154,373 B2 | 10/2021 | Abbott et al. |
| 11,173,003 B2 | 11/2021 | Cassell et al. |
| 11,200,980 B2 | 12/2021 | Beira et al. |
| 11,207,143 B2 | 12/2021 | Abbott et al. |
| 11,234,782 B2 | 2/2022 | Devengenzo et al. |
| 11,278,364 B2 | 3/2022 | Cooper et al. |
| 11,291,442 B2 | 4/2022 | Wixey et al. |
| 11,324,619 B1 | 5/2022 | Yacoby et al. |
| 11,337,716 B2 | 5/2022 | Beira |
| 11,389,259 B2 | 7/2022 | Dachs, II |
| 11,399,886 B2 | 8/2022 | Kerver et al. |
| 11,432,893 B2 | 9/2022 | Itkowitz et al. |
| 11,478,315 B2 | 10/2022 | Beira |
| 11,490,977 B2 | 11/2022 | Schena et al. |
| 11,490,978 B2 | 11/2022 | Klein et al. |
| 11,510,745 B2 | 11/2022 | Chassot et al. |
| 11,547,506 B2 | 1/2023 | Devengenzo et al. |
| 11,564,760 B2 | 1/2023 | Steger et al. |
| 11,571,195 B2 | 2/2023 | Beira |
| 11,607,281 B2 | 3/2023 | Turner |
| 11,627,948 B2 | 4/2023 | Brisson et al. |
| 11,633,246 B2 | 4/2023 | Cavalier et al. |
| 11,633,249 B2 | 4/2023 | Smaby et al. |
| 11,648,076 B2 | 5/2023 | Bailey |
| 11,659,978 B2 | 5/2023 | Larkin et al. |
| 11,660,154 B2 | 5/2023 | Miller et al. |
| 11,672,621 B2 | 6/2023 | Hulford et al. |
| 11,766,303 B2 | 9/2023 | Devengenzo et al. |
| 11,793,585 B2 | 10/2023 | Cassell et al. |
| 11,806,016 B2 | 11/2023 | Ragosta et al. |
| 11,826,017 B2 | 11/2023 | Diolaiti et al. |
| 11,859,967 B2 | 1/2024 | Diolaiti |
| 11,911,069 B2 | 2/2024 | Lambrecht et al. |
| 11,934,594 B2 | 3/2024 | Diolaiti et al. |
| 11,960,665 B2 | 4/2024 | Bailey et al. |
| 11,969,889 B2 | 4/2024 | Cooper et al. |
| 11,974,826 B2 | 5/2024 | Steger et al. |
| 11,974,827 B2 | 5/2024 | Gomez et al. |
| 12,016,646 B2 | 6/2024 | Itkowitz et al. |
| 12,089,809 B2 | 9/2024 | Larkin et al. |
| 12,161,438 B2 | 12/2024 | Chassot et al. |
| 2001/0013764 A1 | 8/2001 | Blumenkranz et al. |
| 2001/0031983 A1* | 10/2001 | Brock .......... A61B 34/71 606/205 |
| 2002/0040217 A1 | 4/2002 | Jinno |
| 2002/0049367 A1 | 4/2002 | Irion et al. |
| 2002/0058929 A1 | 5/2002 | Green |
| 2002/0072736 A1 | 6/2002 | Tierney et al. |
| 2002/0082612 A1 | 6/2002 | Moll et al. |
| 2003/0013949 A1 | 1/2003 | Moll et al. |
| 2003/0060927 A1 | 3/2003 | Gerbi et al. |
| 2003/0155747 A1 | 8/2003 | Bridges |
| 2003/0208186 A1 | 11/2003 | Moreyra |
| 2003/0216715 A1 | 11/2003 | Moll et al. |
| 2004/0049205 A1 | 3/2004 | Lee et al. |
| 2004/0116906 A1 | 6/2004 | Lipow |
| 2004/0236316 A1 | 11/2004 | Danitz et al. |
| 2004/0253079 A1 | 12/2004 | Sanchez |
| 2005/0096502 A1 | 5/2005 | Khalili |
| 2005/0204851 A1 | 9/2005 | Morley et al. |
| 2005/0240078 A1 | 10/2005 | Kwon et al. |
| 2006/0043698 A1 | 3/2006 | Bridges |
| 2006/0079884 A1 | 4/2006 | Manzo et al. |
| 2006/0178559 A1 | 8/2006 | Kumar et al. |
| 2006/0183975 A1 | 8/2006 | Saadat et al. |
| 2006/0219065 A1 | 10/2006 | Jinno et al. |
| 2006/0235436 A1 | 10/2006 | Anderson et al. |
| 2006/0253109 A1 | 11/2006 | Chu |
| 2007/0088340 A1 | 4/2007 | Brock et al. |
| 2007/0137371 A1 | 6/2007 | Devengenzo et al. |
| 2007/0142969 A1* | 6/2007 | Devengenzo .......... A61B 34/71 700/245 |
| 2007/0156123 A1 | 7/2007 | Moll et al. |
| 2007/0208375 A1 | 9/2007 | Nishizawa et al. |
| 2007/0299387 A1 | 12/2007 | Williams et al. |
| 2008/0035857 A1* | 2/2008 | Struye .......... G21K 4/00 250/458.1 |
| 2008/0039255 A1 | 2/2008 | Jinno et al. |
| 2008/0046122 A1* | 2/2008 | Manzo .......... A61B 90/98 700/245 |
| 2008/0058776 A1 | 3/2008 | Jo et al. |
| 2008/0071208 A1 | 3/2008 | Voegele et al. |
| 2008/0103492 A1 | 5/2008 | Morley et al. |
| 2008/0177285 A1* | 7/2008 | Brock .......... A61B 34/71 606/1 |
| 2008/0243106 A1 | 10/2008 | Coe et al. |
| 2008/0287926 A1 | 11/2008 | Abou El Kheir |
| 2008/0314181 A1 | 12/2008 | Schena |
| 2009/0030449 A1 | 1/2009 | Kawai et al. |
| 2009/0036902 A1 | 2/2009 | DiMaio et al. |
| 2009/0088775 A1* | 4/2009 | Swarup .......... A61B 34/71 700/264 |
| 2009/0192522 A1 | 7/2009 | Blumenkranz |
| 2009/0198253 A1 | 8/2009 | Omori |
| 2009/0216248 A1 | 8/2009 | Uenohara et al. |
| 2009/0216249 A1* | 8/2009 | Jinno .......... A61B 34/70 606/130 |
| 2009/0247821 A1 | 10/2009 | Rogers |
| 2009/0248039 A1 | 10/2009 | Cooper et al. |
| 2009/0275994 A1 | 11/2009 | Phan et al. |
| 2009/0299141 A1 | 12/2009 | Downey et al. |
| 2009/0326552 A1* | 12/2009 | Diolaiti .......... A61B 90/10 606/130 |
| 2010/0004508 A1 | 1/2010 | Naito et al. |
| 2010/0011900 A1 | 1/2010 | Burbank |
| 2010/0023025 A1 | 1/2010 | Zeiner et al. |
| 2010/0082041 A1 | 4/2010 | Prisco |
| 2010/0094130 A1 | 4/2010 | Ninomiya et al. |
| 2010/0121347 A1 | 5/2010 | Jaspers |
| 2010/0160929 A1* | 6/2010 | Rogers .......... A61B 34/30 606/130 |
| 2010/0160940 A1 | 6/2010 | Lutze et al. |
| 2010/0170519 A1 | 7/2010 | Romo et al. |
| 2010/0225209 A1 | 9/2010 | Goldberg et al. |
| 2010/0234857 A1 | 9/2010 | Itkowitz et al. |
| 2010/0262162 A1 | 10/2010 | Omori |
| 2010/0286712 A1 | 11/2010 | Won et al. |
| 2010/0305595 A1 | 12/2010 | Hermann |
| 2010/0318099 A1 | 12/2010 | Itkowitz et al. |
| 2010/0318101 A1 | 12/2010 | Choi |
| 2010/0324551 A1 | 12/2010 | Gerhardt |
| 2010/0331859 A1 | 12/2010 | Omori |
| 2011/0082462 A1 | 4/2011 | Suarez et al. |
| 2011/0087236 A1 | 4/2011 | Stokes et al. |
| 2011/0087238 A1 | 4/2011 | Wang et al. |
| 2011/0152881 A1 | 6/2011 | Conner et al. |
| 2011/0213346 A1 | 9/2011 | Morley et al. |
| 2011/0230867 A1 | 9/2011 | Hirschfeld et al. |
| 2011/0275901 A1 | 11/2011 | Shelton, IV |
| 2011/0276084 A1 | 11/2011 | Shelton, IV |
| 2011/0282491 A1 | 11/2011 | Prisco et al. |
| 2011/0290854 A1 | 12/2011 | Timm et al. |
| 2011/0301419 A1 | 12/2011 | Craft et al. |
| 2012/0010628 A1 | 1/2012 | Cooper et al. |
| 2012/0027762 A1 | 2/2012 | Schofield |
| 2012/0031114 A1 | 2/2012 | Mueller et al. |
| 2012/0049623 A1 | 3/2012 | Nakayama |
| 2012/0080040 A1 | 4/2012 | Skora et al. |
| 2012/0095298 A1 | 4/2012 | Stefanchik et al. |
| 2012/0116163 A1 | 5/2012 | Lutze et al. |
| 2012/0132018 A1 | 5/2012 | Tang et al. |
| 2012/0143173 A1 | 6/2012 | Steege et al. |
| 2012/0158014 A1 | 6/2012 | Stefanchik et al. |
| 2012/0191245 A1 | 7/2012 | Fudaba et al. |
| 2012/0209292 A1 | 8/2012 | Devengenzo et al. |
| 2012/0232339 A1 | 9/2012 | Csiky |
| 2012/0253326 A1 | 10/2012 | Kleyman |
| 2012/0277762 A1 | 11/2012 | Lathrop et al. |
| 2012/0283745 A1 | 11/2012 | Goldberg et al. |
| 2012/0289973 A1 | 11/2012 | Prisco et al. |
| 2012/0289974 A1 | 11/2012 | Rogers et al. |
| 2012/0296341 A1 | 11/2012 | Seibold et al. |

(56) References Cited

U.S. PATENT DOCUMENTS

| | | |
|---|---|---|
| 2013/0123805 A1 | 5/2013 | Park et al. |
| 2013/0144274 A1 | 6/2013 | Stefanchik et al. |
| 2013/0172713 A1 | 7/2013 | Kirschenman |
| 2013/0172906 A1 | 7/2013 | Olson et al. |
| 2013/0245643 A1 | 9/2013 | Woodard, Jr. et al. |
| 2013/0245647 A1 | 9/2013 | Martin et al. |
| 2013/0282027 A1 | 10/2013 | Woodard, Jr. et al. |
| 2013/0303408 A1 | 11/2013 | Indermuhle |
| 2013/0304070 A1 | 11/2013 | Nelson et al. |
| 2013/0304083 A1 | 11/2013 | Kaercher et al. |
| 2013/0304084 A1 | 11/2013 | Beira et al. |
| 2014/0005681 A1 | 1/2014 | Gee et al. |
| 2014/0018447 A1 | 1/2014 | McGovern et al. |
| 2014/0018780 A1 | 1/2014 | Hirscheld |
| 2014/0018960 A1 | 1/2014 | Itkowitz |
| 2014/0039527 A1 | 2/2014 | Avelar et al. |
| 2014/0052152 A1 | 2/2014 | Au et al. |
| 2014/0076088 A1 | 3/2014 | Berkelman et al. |
| 2014/0114481 A1 | 4/2014 | Ogawa et al. |
| 2014/0135794 A1 | 5/2014 | Cau |
| 2014/0142595 A1 | 5/2014 | Awtar et al. |
| 2014/0166023 A1 | 6/2014 | Kishi |
| 2014/0180308 A1 | 6/2014 | Von Grunberg |
| 2014/0188091 A1 | 7/2014 | Vidal et al. |
| 2014/0188159 A1 | 7/2014 | Steege |
| 2014/0195010 A1 | 7/2014 | Beira et al. |
| 2014/0200561 A1 | 7/2014 | Ingmanson et al. |
| 2014/0207150 A1 | 7/2014 | Rosa et al. |
| 2014/0229007 A1 | 8/2014 | Kishi |
| 2014/0230595 A1 | 8/2014 | Butt et al. |
| 2014/0249546 A1 | 9/2014 | Shvartsberg et al. |
| 2014/0263541 A1 | 9/2014 | Leimbach et al. |
| 2014/0263553 A1 | 9/2014 | Leimbach et al. |
| 2014/0276950 A1 | 9/2014 | Smaby et al. |
| 2014/0276951 A1 | 9/2014 | Hourtash et al. |
| 2014/0276956 A1 | 9/2014 | Crainich et al. |
| 2014/0277017 A1 | 9/2014 | Leimbach et al. |
| 2014/0277203 A1 | 9/2014 | Atoulikian et al. |
| 2014/0340796 A1 | 11/2014 | Sandhu et al. |
| 2014/0350570 A1 | 11/2014 | Lee |
| 2015/0057499 A1 | 2/2015 | Erden et al. |
| 2015/0057702 A1 | 2/2015 | Edmondson et al. |
| 2015/0060517 A1 | 3/2015 | Williams |
| 2015/0066018 A1 | 3/2015 | Doll et al. |
| 2015/0105821 A1 | 4/2015 | Ward et al. |
| 2015/0113933 A1 | 4/2015 | Markt |
| 2015/0142018 A1 | 5/2015 | Sniffin et al. |
| 2015/0150575 A1 | 6/2015 | Hartoumbekis et al. |
| 2015/0173840 A1 | 6/2015 | Lohmeier |
| 2015/0230869 A1 | 8/2015 | Shim et al. |
| 2015/0250547 A1 | 9/2015 | Fukushima et al. |
| 2015/0265355 A1 | 9/2015 | Prestel et al. |
| 2016/0022365 A1 | 1/2016 | Jensen et al. |
| 2016/0051274 A1 | 2/2016 | Howell et al. |
| 2016/0151115 A1 | 6/2016 | Karguth et al. |
| 2016/0220314 A1 | 8/2016 | Huelman et al. |
| 2016/0270867 A1 | 9/2016 | Scholan |
| 2016/0302876 A1 | 10/2016 | Teichtmann |
| 2016/0303743 A1 | 10/2016 | Rockrohr |
| 2016/0346053 A1 | 12/2016 | Beira |
| 2016/0374766 A1 | 12/2016 | Schuh |
| 2017/0007335 A1 | 1/2017 | Popovic et al. |
| 2017/0020615 A1 | 1/2017 | Koenig et al. |
| 2017/0065364 A1 | 3/2017 | Schuh et al. |
| 2017/0086932 A1 | 3/2017 | Auld et al. |
| 2017/0189130 A1 | 7/2017 | Weir |
| 2017/0215976 A1 | 8/2017 | Nowlin et al. |
| 2017/0245954 A1 | 8/2017 | Beira |
| 2017/0252096 A1 | 9/2017 | Felder et al. |
| 2017/0265951 A1 | 9/2017 | Grover et al. |
| 2017/0273749 A1 | 9/2017 | Grover et al. |
| 2017/0308667 A1 | 10/2017 | Beira et al. |
| 2017/0360522 A1 | 12/2017 | Beira |
| 2017/0367778 A1 | 12/2017 | Beira |
| 2018/0000472 A1 | 1/2018 | Beira |
| 2018/0000544 A1 | 1/2018 | Beira |
| 2018/0000550 A1 | 1/2018 | Beira |
| 2018/0008358 A1 | 1/2018 | Kostrzewski et al. |
| 2018/0028269 A1 | 2/2018 | Morel et al. |
| 2018/0055583 A1 | 3/2018 | Schuh et al. |
| 2018/0078439 A1 | 3/2018 | Cagle et al. |
| 2018/0110576 A1 | 4/2018 | Kopp |
| 2018/0125519 A1 | 5/2018 | Beira et al. |
| 2018/0125592 A1 | 5/2018 | Beira |
| 2018/0168760 A1 | 6/2018 | Koch, Jr. et al. |
| 2018/0214223 A1 | 8/2018 | Turner |
| 2018/0242991 A1 | 8/2018 | Beira |
| 2018/0296286 A1 | 10/2018 | Peine et al. |
| 2018/0353251 A1 | 12/2018 | Cuthbertson et al. |
| 2018/0353252 A1 | 12/2018 | Chassot et al. |
| 2018/0360548 A1 | 12/2018 | Marshall et al. |
| 2019/0029770 A1 | 1/2019 | Bailey |
| 2019/0133698 A1 | 5/2019 | Beira et al. |
| 2019/0239968 A1 | 8/2019 | Beira |
| 2019/0314096 A1 | 10/2019 | Diolaiti et al. |
| 2019/0328473 A1 | 10/2019 | Chassot et al. |
| 2019/0380795 A1 | 12/2019 | Tsao et al. |
| 2020/0105412 A1 | 4/2020 | Beira |
| 2020/0246085 A1 | 8/2020 | Noonan et al. |
| 2020/0268464 A1 | 8/2020 | Beira |
| 2020/0315721 A1 | 10/2020 | Rabindran et al. |
| 2021/0106348 A1 | 4/2021 | Beira |
| 2021/0330407 A1 | 10/2021 | Chassot et al. |
| 2021/0330408 A1 | 10/2021 | Chassot et al. |
| 2022/0280179 A1 | 9/2022 | Beira |
| 2023/0054176 A1 | 2/2023 | Beira |
| 2023/0082915 A1 | 3/2023 | Chassot et al. |
| 2023/0125213 A1 | 4/2023 | Chassot et al. |
| 2024/0000525 A1 | 1/2024 | Cassell et al. |
| 2024/0115334 A1 | 4/2024 | Beira |
| 2024/0335246 A1 | 10/2024 | Chassot et al. |

FOREIGN PATENT DOCUMENTS

| | | |
|---|---|---|
| CN | 101637402 A | 2/2010 |
| CN | 101732093 A | 6/2010 |
| CN | 103717355 A | 4/2014 |
| CN | 107666878 A | 2/2018 |
| DE | 4303311 A1 | 8/1994 |
| DE | 19652792 C2 | 5/1999 |
| DE | 10314827 B3 | 4/2004 |
| DE | 10314828 B3 | 7/2004 |
| DE | 102012222755 A1 | 6/2014 |
| DE | 102014205036 A1 | 9/2015 |
| DE | 102014205159 A1 | 9/2015 |
| EP | 0085609 B1 | 7/1987 |
| EP | 0595291 A1 | 5/1994 |
| EP | 0621009 A1 | 10/1994 |
| EP | 0677275 A2 | 10/1995 |
| EP | 0776739 A2 | 6/1997 |
| EP | 1254642 A1 | 11/2002 |
| EP | 1279371 B1 | 12/2004 |
| EP | 1886630 A2 | 2/2008 |
| EP | 1889579 A2 | 2/2008 |
| EP | 1889583 A1 | 2/2008 |
| EP | 2058090 A2 | 5/2009 |
| EP | 1977677 B1 | 8/2009 |
| EP | 2095778 A1 | 9/2009 |
| EP | 1889583 B1 | 4/2011 |
| EP | 2377477 B1 | 5/2012 |
| EP | 2473119 A2 | 7/2012 |
| EP | 2305144 B1 | 10/2012 |
| EP | 2044893 B1 | 7/2013 |
| EP | 2653110 A1 | 10/2013 |
| EP | 2679192 A2 | 1/2014 |
| EP | 2736680 A2 | 6/2014 |
| EP | 2777561 A1 | 9/2014 |
| EP | 2783643 A1 | 10/2014 |
| EP | 2837340 A1 | 2/2015 |
| EP | 2837354 A1 | 2/2015 |
| EP | 2554131 B1 | 8/2015 |
| EP | 2777561 B1 | 10/2015 |
| EP | 2979657 A1 | 2/2016 |
| EP | 2837340 B1 | 10/2016 |

(56) References Cited

FOREIGN PATENT DOCUMENTS

| | | |
|---|---|---|
| EP | 2783643 B1 | 1/2019 |
| GB | 834244 A | 5/1960 |
| GB | 969899 A | 9/1964 |
| JP | H06122299 A | 5/1994 |
| JP | 2001504395 A | 4/2001 |
| JP | 2004041580 A | 2/2004 |
| JP | 2007061946 A | 3/2007 |
| JP | 2007290096 A | 11/2007 |
| JP | 2008104620 A | 5/2008 |
| JP | 2009018027 A | 1/2009 |
| JP | 2011194163 A | 10/2011 |
| JP | 2013035117 A | 2/2013 |
| JP | 2015024036 A | 2/2015 |
| JP | 2015128681 A | 7/2015 |
| JP | 2015150425 A | 8/2015 |
| JP | 2015526115 A | 9/2015 |
| JP | 2016519585 A | 7/2016 |
| KR | 20110032444 A | 3/2011 |
| KR | 20130031403 A | 3/2013 |
| KR | 101645969 B1 | 8/2016 |
| SU | 722754 A1 | 3/1980 |
| WO | WO-8200611 A1 | 3/1982 |
| WO | WO-9639944 A1 | 12/1996 |
| WO | WO-9743942 A1 | 11/1997 |
| WO | WO-9825666 A1 | 6/1998 |
| WO | WO-0134017 A2 | 5/2001 |
| WO | WO-0197717 A1 | 12/2001 |
| WO | WO-03067341 A2 | 8/2003 |
| WO | WO-03086219 A2 | 10/2003 |
| WO | WO-2004052171 A2 | 6/2004 |
| WO | WO-2005009482 A2 | 2/2005 |
| WO | WO-2005046500 A1 | 5/2005 |
| WO | WO-2006086663 A2 | 8/2006 |
| WO | WO-2007133065 A1 | 11/2007 |
| WO | WO-2007146987 A2 | 12/2007 |
| WO | WO-2008070556 A1 | 6/2008 |
| WO | WO-2008130235 A2 | 10/2008 |
| WO | WO-2009091497 A2 | 7/2009 |
| WO | WO-2009095893 A2 | 8/2009 |
| WO | WO-2009145572 A2 | 12/2009 |
| WO | WO-2009157719 A2 | 12/2009 |
| WO | WO-2010019001 A2 | 2/2010 |
| WO | WO-2010030114 A2 | 3/2010 |
| WO | WO-2010050771 A2 | 5/2010 |
| WO | WO-2010083480 A2 | 7/2010 |
| WO | WO-2010096580 A1 | 8/2010 |
| WO | WO-2010130817 A1 | 11/2010 |
| WO | WO-2011025818 A1 | 3/2011 |
| WO | WO-2011027183 A2 | 3/2011 |
| WO | WO-2011123669 A1 | 10/2011 |
| WO | WO-2012020386 A1 | 2/2012 |
| WO | WO-2012049623 A1 | 4/2012 |
| WO | WO-2013007784 A1 | 1/2013 |
| WO | WO-2013014621 A2 | 1/2013 |
| WO | WO-2013018934 A1 | 2/2013 |
| WO | WO-2014012780 A1 | 1/2014 |
| WO | WO-2014018447 A1 | 1/2014 |
| WO | WO-2014067804 A1 | 5/2014 |
| WO | WO-2014094716 A1 | 6/2014 |
| WO | WO-2014094717 A1 | 6/2014 |
| WO | WO-2014094718 A1 | 6/2014 |
| WO | WO-2014094719 A1 | 6/2014 |
| WO | WO-2014114551 A1 | 7/2014 |
| WO | WO-2014139023 A1 | 9/2014 |
| WO | WO-2014145148 A2 | 9/2014 |
| WO | WO-2014156221 A1 | 10/2014 |
| WO | WO-2014166573 A1 | 10/2014 |
| WO | WO-2014201010 A1 | 12/2014 |
| WO | WO-2014201538 A1 | 12/2014 |
| WO | WO-2015081946 A1 | 6/2015 |
| WO | WO-2015081947 A1 | 6/2015 |
| WO | WO-2015088647 A1 | 6/2015 |
| WO | WO-2015088655 A1 | 6/2015 |
| WO | WO-2015111475 A1 | 7/2015 |
| WO | WO-2015113933 A1 | 8/2015 |
| WO | WO-2015129383 A1 | 9/2015 |
| WO | WO-2015139674 A1 | 9/2015 |
| WO | WO-2015175200 A1 | 11/2015 |
| WO | WO-2016030767 A1 | 3/2016 |
| WO | WO-2016083189 A1 | 6/2016 |
| WO | WO-2016097861 A1 | 6/2016 |
| WO | WO-2016097864 A2 | 6/2016 |
| WO | WO-2016097868 A1 | 6/2016 |
| WO | WO-2016097871 A1 | 6/2016 |
| WO | WO-2016097873 A2 | 6/2016 |
| WO | WO-2016154173 A1 | 9/2016 |
| WO | WO-2016162751 A1 | 10/2016 |
| WO | WO-2016162752 A1 | 10/2016 |
| WO | WO-2016183054 A1 | 11/2016 |
| WO | WO-2016189284 A1 | 12/2016 |
| WO | WO-2016209891 A1 | 12/2016 |
| WO | WO-2017015599 A1 | 1/2017 |
| WO | WO-2017037532 A1 | 3/2017 |
| WO | WO-2017064301 A1 | 4/2017 |
| WO | WO-2017064303 A1 | 4/2017 |
| WO | WO-2017064305 A1 | 4/2017 |
| WO | WO-2017064306 A1 | 4/2017 |
| WO | WO-2017134077 A1 | 8/2017 |
| WO | WO-2017220978 A1 | 12/2017 |
| WO | WO-2018142112 A1 | 8/2018 |
| WO | WO-2018162921 A1 | 9/2018 |
| WO | WO-2018207136 A1 | 11/2018 |
| WO | WO-2019099346 A2 | 5/2019 |
| WO | WO-2019155383 A1 | 8/2019 |
| WO | WO-2020131304 A1 | 6/2020 |
| WO | WO-2020141487 A2 | 7/2020 |
| WO | WO-2020263870 A1 | 12/2020 |
| WO | WO-2023073565 A1 | 5/2023 |

OTHER PUBLICATIONS

Abbott, et al., Design of an Endoluminal Notes Robotic System, IEEE/RSJ International Conference on Intelligent Robots and Systems, 2007, San Diego, CA (pp. 410-416).

Aesculap Surgical Technologies, Aesculap.RTM. Caiman.RTM., Advanced Bipolar Seal and Cut Technology Brochure, 6 pages (retrieved Aug. 31, 2015).

Arata, et al., Development of a dexterous minimally-invasive surgical system with augmented force feedback capability, IEEE/RSJ International Conference on Intelligent Robots and Systems, 2005 (pp. 3207-3212).

Cavusoglu, et al., Laparoscopic Telesurgical Workstation, IEEE Transactions on Robotics and Automation, (15)4:728-739 (1999).

Charles, et al., Dexterity-enhanced Telerobotic Microsurgery, 8th International Conference Advanced Robotics, pp. 5-10 (1997).

Dachs, et al., Novel Surgical Robot Design: Minimizing the Operating Envelope With in the Sterile Field, 28th International Conference, IEEE Engineering in Medicine Biology Society, 2006, New York (pp. 1505-1508).

Dario, et al., "Novel Mechatronic Tool for Computer-Assisted Arthroscopy," IEEE Transactions on Information Technology in Biomedicine, 4(1):15-29 (Mar. 2000).

Extended European Search Report dated Mar. 18, 2020 in EP Patent Appl. Serial No. 19213231.4 (1031).

Focacci, et al., Lightweight Hand-held Robot for Laparoscopic Surgery, IEEE International Conference on Robotics & Automation, Rome, Italy, pp. 599-604 (2007).

Guthart, et al., The Intuitive. TM. Telesurgery System: Overview and Application, IEEE International Conference on Robotics & Automation, San Francisco, CA, 2000 (pp. 618-621).

Ikuta, et al., Development of Remote Microsurgery Robot and New Surgical Procedure for Deep and Narrow Space, IEEE International Conference on Robotics & Automation, Taipei, Taiwan, 2003 (pp. 1103-1108).

Ikuta, et al., Hyper Redundant Miniature Manipulator 'Hyper Finger' for Remote Minimally Invasive Surgery in Deep Area, IEEE International Conference on Robotics & Automation, Taipei, Taiwan, 2003 (pp. 1098-1102).

International Search Report & Written Opinion dated Feb. 2, 2017 in Int'l PCT Patent Appl. Serial No. PCT/IB2016/001286.

(56) References Cited

OTHER PUBLICATIONS

International Search Report & Written Opinion dated Jan. 18, 2013 in Int'l PCT Patent Appl. Serial No. PCT/IB2012/053786.
International Search Report & Written Opinion dated Jul. 10, 2018 in Int'l PCT Patent Appl. Serial No. PCT/IB2018/053272.
International Search Report & Written Opinion dated Jun. 10, 2016 in Int'l PCT Patent Appl. Serial No. PCT/IB2015/002533.
International Search Report & Written Opinion dated Jun. 13, 2016 in Int'l PCT Patent Appl. Serial No. PCT/IB2015/002493.
International Search Report & Written Opinion dated Mar. 30, 2015 in Int'l PCT Patent Appl. Serial No. PCT/EP2015/051473.
International Search Report & Written Opinion dated May 23, 2016 in Int'l PCT Patent Appl. Serial No. PCT/IB2015/002524.
International Search Report & Written Opinion dated May 24, 2016 in Int'l PCT Patent Appl. Serial No. PCT/IB2015/002487.
International Search Report & Written Opinion dated Sep. 2, 2016 in Int'l PCT Patent Appl. Serial No. PCT/IB2016/000543.
International Search Report & Written Opinion dated Feb. 17, 2016 in Int'l PCT Patent Appl. Serial No. PCT/IB2015/002095.
International Search Report & Written Opinion dated Mar. 23, 2012 in Int'l PCT Patent Appl. Serial No. PCT/IB2011/054476.
International Search Report & Written Opinion dated Apr. 26, 2016 in Int'l PCT Patent Appl. Serial No. PCT/IB2015/002512.
International Search Report & Written Opinion dated Jul. 7, 2020 in Int'l. PCT Patent Appl. Serial No. PCTIB2020050039.
International Search Report & Written Opinion dated Jul. 23, 2019 in Int'l PCT Patent Appl. Serial No. PCT/IB2019/050961.
International Search Report & Written Opinion dated Aug. 25, 2016 in Int'l PCT Patent Appl. Serial No. PCT/IB2016/000542.
Ishii, et al., Development of a New Bending Mechanism and Its Application to Robotic Forceps Manipulator, IEEE International Conference on Robotics & Automation, Rome, Italy, 2007 (pp. 238-243).
Kobayashi, et al., Small Occupancy Robotic Mechanisms for Endoscopic Surgery, International Conference on Medical Image Computing and Computer assisted Interventions, 2002, (pp. 75-82).
Lang, et al., Intra-operative robotics: NeuroArm., Acta Neurochir Suppl, 109:231-236 (2011).
Mayer, et al., The Endo[PA]R System for Minimally Invasive Robotic Surgery, IEEE/RSJ International Conference on Intelligent Robots and Systems, Sendai, Japan, 2004 (pp. 3637-3642).
Mitsuishi, et al., Development of a Remote Minimally Invasive Surgical System with Operational Environment Transmission Capability, IEEE International Conference on Robotics & Automation, Taipei, Taiwan, 2003, (pp. 2663-2670).
Mitsuishi, et al., Master-Slave Robotic Platform and its Feasibility Study for Micro-Neurosurgery, Int. J. Med. Robot., 9(2):180-9 (2013).
Morita, et al., Microsurgical Robotic System for the Deep Surgical Field: development of a Prototype and Feasibility Studies in Animal and Cadaveric Models, J. Neurosurg., 103(2):320-7 (2005).
Nakamura, et al., Multi-DOF Forceps Manipulator System for Laparoscopic Surgery-Mechanism miniaturized & Evaluation of New Interface, 4th International Conference on Medical Image Computing and Computer assisted Interventions (MICCAI2001), 2001 (pp. 606-613).
Peirs, et al., "Design of an Advanced Tool Guiding System for Robotic Surgery," IEEE International Conference on Robotics & Automation, Taipei, Taiwan, 2003, (pp. 2651-2656).
Salle, et al., Optimal Design of High Dexterity Modular MIS Instrument for Coronary Artery Bypass Grafting, IEEE International Conference on Robotics & Automation, New Orleans, LA, 2004, (pp. 1276-1281).
Seibold, et al., Prototype of Instrument for Minimally Invasive Surgery with 6-Axis Force Sensing Capability, IEEE International Conference on Robotics & Automation, Barcelona, Spain, 2005, (pp. 496-501).

Simaan, et al., Dexterous System for Laryngeal Surgery: Multi-Backbone Bending Snake-like Slaves for Teleoperated Dexterous Surgical Tool Manipulation, IEEE International Conference on Robotics & Automation, New Orleans, LA, 2004 (pp. 351-357).
Stryker(TM), Endoscopy, Take a Look Around, Ideal Eyes. TM. FFD122 HD, Articulating Laparoscope Brochure, 2 pages (2009).
Swiss Search Report dated Jun. 4, 2012 in Swiss Patent Application No. CH 00702/12.
Tavakoli, et al., Force Reflective Master-Slave System for Minimally Invasive Surgery, IEEE/RSJ International Conference on Intelligent Robots and Systems, Las Vegas, NV, 2003, (pp. 3077-3082).
Taylor, et al., Steady-Hand Robotic System for Microsurgical Augmentation, The International Journal of Robotics Research, 18(12):1201-1210 (1999).
www.cttc.co/technologies/maestro-non-robotic-dexterous-laproscopic-instrum- ent-writs-providing-seven-degrees, Maestro: Non-Robotic Dexterous Laproscopic Instrument With a Wrist Providing Seven Degrees of Freedom, accessed Nov. 12, 2015, 4 pages.
Yamashita, et al., Development of Endoscopic Forceps Manipulator Using Multi-Slider Linkage Mechanisms, The 1st Asian Symposium on Computer Aided Surgery-Robotic and Image-Guided Surgery, Ibaraki, Japan, 4 pages (2005).
Zeus, Robotic Surgical System, available at http://allaboutroboticsurgery.com/zeusrobot.html.
U.S. Appl. No. 13/878,924 / U.S. Pat. No. 10,092,359, filed May 17, 2013 / Oct. 9, 2018.
U.S. Appl. No. 14/233,184 / U.S. Pat. No. 9,696,700, filed Jan. 16, 2014 / Jul. 4, 2017.
U.S. Appl. No. 15/116,509 / U.S. Pat. No. 10,265,129, filed Aug. 3, 2016 / Apr. 23, 2019.
U.S. Appl. No. 15/506,659 / U.S. Pat. No. 10,357,320, filed Feb. 24, 2017 / Jul. 23, 2019.
U.S. Appl. No. 15/536,539 / U.S. Pat. No. 10,864,049, filed Jun. 15, 2017 / Dec. 15, 2020.
U.S. Appl. No. 15/536,562 / U.S. Pat. No. 10,864,052, filed Jun. 15, 2017 / Dec. 15, 2020.
U.S. Appl. No. 15/536,568 / U.S. Pat. No. 10,548,680, filed Jun. 15, 2017 / Feb. 4, 2020.
U.S. Appl. No. 15/536,573 / U.S. Pat. No. 11,039,820, filed Jun. 15, 2017 / Jun. 22, 2021.
U.S. Appl. No. 15/536,576 / U.S. Pat. No. 10,646,294, filed Jun. 15, 2017 / May 12, 2020.
U.S. Appl. No. 15/564,193 / U.S. Pat. No. 10,568,709, filed Oct. 3, 2017 / Feb. 25, 2020.
U.S. Appl. No. 15/564,194 / U.S. Pat. No. 10,363,055, filed Oct. 3, 2017 / Jul. 30, 2019.
U.S. Appl. No. 15/633,611 / U.S. Pat. No. 10,325,072, filed Jun. 26, 2017 / Jun. 18, 2019.
U.S. Appl. No. 15/756,037 / U.S. Pat. No. 10,786,272, filed Feb. 27, 2018 / Sep. 29, 2020.
U.S. Appl. No. 15/976,812 / U.S. Pat. No. 11,058,503, filed May 10, 2018 / Jul. 13, 2021.
U.S. Appl. No. 16/153,695 / U.S. Pat. No. 11,076,922, filed Oct. 5, 2018 / Aug. 3, 2021.
U.S. Appl. No. 16/269,383 / U.S. Pat. No. 10,413,374, filed Feb. 6, 2019 / Sep. 17, 2019.
U.S. Appl. No. 16/389,854, filed Apr. 19, 2019.
U.S. Appl. No. 16/442,435 / U.S. Pat. No. 10,510,447, filed Jun. 14, 2019 / Dec. 17, 2019.
U.S. Appl. No. 16/505,585, filed Jul. 8, 2019.
U.S. Appl. No. 16/701,063, filed Dec. 2, 2019.
U.S. Appl. No. 16/870,870, filed May 8, 2020.
U.S. Appl. No. 17/032,631, filed Sep. 25, 2020.
U.S. Appl. No. 17/351,118, filed Jun. 17, 2021.
U.S. Appl. No. 17/364,246, filed Jun. 30, 2021.
U.S. Appl. No. 17/372,163, filed Jul. 9, 2021.

* cited by examiner

MECHANICAL MANIPULATOR FOR SURGICAL INSTRUMENTS

CROSS-REFERENCE TO RELATED APPLICATIONS

This Application is a continuation of U.S. patent application Ser. No. 16/153,695, filed Oct. 5, 2018, now U.S. Pat. No. 11,076,922, which is a continuation of U.S. patent application Ser. No. 13/878,924, filed May 17, 2013, now U.S. Pat. No. 10,092,359, which is a National Phase of International PCT Patent Application No. PCT/IB2011/054476, filed Oct. 11, 2011, which claims the benefit of European Patent Application No. 10187088.9 and No. 10187097.0, both filed on Oct. 11, 2010, the entire disclosure of each of which is incorporated herein by reference. This application is also a continuation-in-part of U.S. patent application Ser. No. 16/701,063, filed Dec. 2, 2019, now U.S. Pat. No. 10,510,447, which is a continuation of U.S. patent application Ser. No. 16/442,435, filed Jun. 14, 2019, now U.S. Pat. No. 10,510,447, which is a continuation of U.S. patent application Ser. No. 15/633,611, filed Jun. 26, 2017, now U.S. Pat. No. 10,325,072, which is a continuation of U.S. patent application Ser. No. 14/233,184, filed Jan. 16, 2014, now U.S. Pat. No. 9,696,700, which is a National Phase of International PCT Patent Application No. PCT/IB2012/053786, filed Jul. 25, 2012, which claims the benefit of Swiss Patent Application No. CH00702/12, filed May 18, 2012 and U.S. Provisional Patent Application No. 61/511,994, filed Jul. 27, 2011, the entire disclosures of each of which are incorporated herein by reference.

FIELD OF THE INVENTION

The present invention relates to the field of remotely actuated mechanisms and devices for use in surgical procedures within the abdominal cavity, using reduced incisions in the abdominal wall.

BACKGROUND OF THE INVENTION

A major progress in abdominal surgery has occurred during the last decades with the introduction of laparoscopic and minimally invasive techniques. These innovative procedures focused much attention due to their several advantages: smaller abdominal incisions needed, resulting in faster recovery of the patient, improved cosmetics, and shorter stay in the hospital. The safety, efficiency and cost-effectiveness of laparoscopic surgery have subsequently been demonstrated in clinical trials for many routine abdominal operations. However, from the surgeon's point of view, there are still many difficulties in learning and performing such procedures with current laparoscopic equipment, which is non-ergonomic, non-intuitive and missing in adequate stiffness, precision and force feedback.

In order to overcome the disadvantages of traditional minimally invasive surgery (MIS), robot technology has been introduced into the operation room. Although a wide range of diagnostic and therapeutic robotic devices have been developed, the only commercial systems that have already been used in human surgery are the da Vinci System, by Intuitive Surgical, [Guthart2000], and ZEUS, by Computer Motion. Following the fusion between the two companies, the ZEUS robot is no longer produced. The major advantages of these robotic systems are related with the additional degrees of freedom available to the surgeon that allows more complex movements in a limited space, with an increased stiffness. This increased mobility and stiffness has led to short learning curves even for non-laparoscopic surgeons. A major disadvantage of these systems is the high cost of acquisition and maintenance which are actually not affordable for the majority of surgical departments worldwide.

Another drawback of these systems is related with the fact that current surgical robots are voluminous, competing for precious space within the operating room environment and significantly increasing preparation time. Access to the patient is thus impaired and this raises safety concerns. In addition, although robotic systems offer excellent vision and precise tissue manipulation within a defined area, they are limited in operations involving more than one quadrant of the abdomen. Since many gastrointestinal operations involve operating in at least two abdominal quadrants, the repeated disconnection and movement of the robots increase significantly the duration of the surgical procedure.

Despite various existing interesting systems and after several years of surgical instrumentation research, surgical robotics is still only at the very beginning of a very promising large scale development. One of the major open drawbacks is related to the fact that current robotic instruments are still too bulky and have insufficient dexterity for complex surgical procedures.

Further weaknesses of these systems are related with the stiffness, precision and payload capacity of the micro-manipulator units. A large number of conventional and robotic manipulators have been developed [Taylor 1999, Cavusoglu 1999, Mitsuishi2003, Mayer2004, Guthart2000, Tavakoli2003, Seibold2005, Das 1997, Dachs2006, Abbott2007, Ikuta2003, Nakamura2000, Yamashita2005, Arata2005, Salle2004, Kobayashi2002, Dario2000, Peirs2003, Simaan2004, Ikuta2003, Focacci2007, Ishii2007] but their size, dexterity, stiffness, precision and payload capacity are not completely fulfilling the needs for MIS. In some cases, these insufficiencies lead to increased operative time or imprecise performance of several surgical tasks.

Other prior art documents include the following publications: US 2005/0096502, US 2009/0247821, GB 969,899, JP 2008-104620, U.S. Pat. No. 6,197,017, US 2002/0049367, US 2003/0208186, US 2005/0240078, US 2006/0183975, US 2007/0299387, EP 0 595 291, U.S. Pat. No. 6,233,504, US 2004/0236316, US 2004/0253079, US 2008/0058776, US 2008/0314181, US 2009/0198253, WO 03/067341, WO 2004/052171, WO 2005/046500, WO 2007/133065, WO 2008/130235, WO 03/086219, WO 2010/030114, DE 10314827, JP 2004041580, WO 2010/050771, WO 2010/019001, WO 2009/157719, WO 2009/145572, WO 2010/096580, DE 10314828, WO 2010/083480, U.S. Pat. No. 5,599,151, EP 1 254 642, CN 101584594, CN 101732093, U.S. Pat. No. 5,810,716, DE 4303311, US 2008/071208, US 2006/253109, WO 2009/095893, WO 2005/009482, CN 101637402, EP 0 621 009, WO 2009/091497, WO 2006/086663, EP 2 058 090.

SUMMARY OF THE INVENTION

A first aim of the present invention is to improve the known devices and systems.

A further aim of the present invention is to provide a mechanical system, based on a new cable driven mechanical transmission, able to provide sufficient dexterity, stiffness, speed, precision and payload capacity to actuate multi-DOF (degrees of freedom) micro-manipulators. Besides the possibility of being used in several articulated surgical instruments and robotic systems for surgery or other applications involving remote manipulation, it enables the design of a fully mechanical surgical instrument, which offers the advantages of conventional laparoscopy (low cost, tactile feedback, high payload capacity) combined with the advantages of single port surgery (single incision, scarless surgery, navigation through several quadrants of the abdominal cavity) and robotic surgery (greater degrees of freedom, short learning curve, high stiffness, increased intuition).

The unique design of the proposed system provides an intuitive user interface to achieve such enhanced manoeuvrability, allowing each joint of a teleoperated slave system to be driven by controlling the position of a mechanically connected master unit.

The design and performance specifications of this system were driven by surgical task requirements and its use can contribute to increase the performance of abdominal surgical procedures, increasing their reliability.

The mechanical design of micro-mechanical systems can be performed according to many possible concepts and options, even if the kinematical architecture has already been defined and size and shape specifications imposed. One of the main issues is related with the design of a proper actuation and transmission system. In case of micro-mechanical systems for minimally invasive surgery, and especially for the endoscopic units, this aspect is crucial because the working space and incision dimensions are extremely limited and the high dexterity kinematics and demanding performance constraints are tough design goals to be pursued, since the micro mechanisms should meet highly demanding requirements of stability, precision, force and speed to effectively perform a surgical task. Given that, a special effort was placed in the study and development of a novel mechanical transmission, able to meet all those specified requirements.

The invention concerns a mechanism for remote manipulation comprising:
 a. a plurality of movable links; and
 b. a plurality of actuated joints placed between the said links, in a serial, parallel or hybrid configuration; and
 c. a plurality of joint driven pulleys, placed on each said actuated joint, with the axis co-linear with the axis of the respective joint, actuating different degrees of freedom of the mechanism; and
 d. a plurality of actuation pulleys, remotely placed relatively to the movable links of the said mechanism wherein the actuation commands are transmitted to said driven pulleys by means of a cable driven mechanical transmission; and
 e. said cable driven mechanical transmission comprising a plurality of driving cables, each coupling an actuation pulley at a proximal location of the mechanism and another one of said joint driven pulley, and wherein at least one of said joints is a co-axial joint where the axis of adjoining links are aligned or in a parallel configuration.

In an embodiment, each said driving cable may comprise a closed loop cable system, transmitting the actuation motion from the said actuation pulleys to the joint driven pulleys.

In an embodiment, each said coaxial joint(s) may comprise an idler tube which is coaxial with the joint axis and which is able to rotate around its axis.

In an embodiment, said closed loop cable may comprise a single ended cable, whose both extremities are linked to said actuated pulley or said joint driven idler pulley or said idler tube for transmission of the controlled motion by contact force.

In an embodiment, said closed loop cable may comprise two ended cables, whose extremities are attached in the said actuated pulleys, said joint driven idler pulleys or said idler tubes.

In an embodiment, at least one of said actuated joints may be of pivot type, where the axis of the said adjoining links are not alignment and the angle between them and changes with the movement of the actuated joint.

In an embodiment each said co-axial joint may comprise one joint idler tube per degree of freedom of the mechanism and each said joint idler tube are co-linear with the axis of the respective said coaxial joint.

In an embodiment, the axis of each said idler tube may keep its co-linear position by means of a set of external ball bearings.

In an embodiment, the axial position of each said idler tube may be kept, in relation to the other idler tubes of the same co-axial joint, by means of the contact between one or more parts of the idler tube, namely radial flanges or extremities, with external ball bearings or bushing components or any other component of the mechanism.

In an embodiment, the transmission of the actuated motion between the different stages of closed cable loops and the respective joint idler tubes may be done through the force generated on the fixation of the cable extremities.

In an embodiment, the transmission of the actuated motion between the different stages of closed loop cables, for the same said closed loop cable system, and the respective said joint idler tubes may be done through the contact force generated between them.

In an embodiment, said contact force may be increased by increasing the number of cable turns around the said joint idler tubes.

In an embodiment, said contact force may be increased by the use of a chain or flexible timing belt element or any other flexible transmission element.

In an embodiment, the chain or flexible element may be a bead chain, comprising a cable with several spherical or other axisymmetric elements, spaced by a constant pitch, along the segments of the cable that contact said joint idler tubes.

In an embodiment, the joint idler tubes, idler pulleys, actuation pulleys and joint driven pulleys may comprise grooves and specially shaped holes to hold said chain or flexible belt element and said spherical or other axisymmetric elements, increasing the transmitted force.

In an embodiment, the actuation pulleys may receive the input control commands.

In an embodiment, the input commands may be given by an operator moving directly the actuated pulleys.

In an embodiment, the input commands may be given by an operator moving a mechanical system that promotes the rotation of the said actuated pulleys.

In an embodiment, the input commands may be given by a plurality of actuators, controlled by electrical signals, to selectively drive the distal part of the mechanism.

In an embodiment, the forces experienced by the distal part of the mechanism are reproduced at the said actuated pulleys to provide force feedback.

In an embodiment, the invention concerns a device comprising a mechanism as defined in the different embodiments defined herein.

In an embodiment, the device is a mechanical teleoperated surgical system, comprising:

a rigid support tube, having two extremities, a distal one, which is inside the patient's body during the surgical procedure, and a proximal one, which is located outside the patient's body; and a slave articulated unit, coupled to said distal portion of said support tube, composed by two miniature serial manipulators, sharing the same proximal shoulder component, said proximal shoulder component coupled to the said distal portion of the support tube by a rotational joint whose axis is perpendicular to the said support tube's axis, each said miniature serial manipulator comprising a plurality of linkages and joints and a distal griping end-effector element;

a master articulated unit, placed in the distal extremity of the said support tube, composed by two serial manipulators, each one having a plurality of linkages and joints and a distal input handle, with exactly the same kinematics and cable transmission topology of the said slave manipulators, wherein input commands from an operator cause the movement of said slave's end-effectors according to said input commands; and a cable driven mechanical transmission system, coupled between said master and said slave manipulators, for precisely emulating movement of said master manipulators by said slave manipulators, wherein each driven pulley, actuating a certain degree of freedom, of the said master manipulators is connected to the driven pulley of the said slave manipulator actuating the same degree of freedom; and a stereoscopic image capture component positioned at the distal end of the guide tube; and distal surgical instruments, attached to the end-effectors of the slave manipulators.

The surgical instruments may be of any type suitable to be used with the present invention and systems.

In an embodiment, the miniature serial manipulator has an anthropomorphic kinematics, resembling the human arm, said miniature serial manipulator comprising:

a first distal joint, coupled to said distal end of said proximal shoulder component, said first distal joint having a first joint axis substantially co-axial to said proximal shoulder component axis, a first distal link movably coupled to said first distal joint, a second distal joint coupled to said first distal joint via said first distal link, said second distal joint having a second joint axis substantially perpendicular and intersecting to said first joint axis, a second distal link movably coupled to said second distal joint, a third distal joint coupled to said second distal joint via said second distal link, said third distal joint having a third joint axis substantially parallel to said second joint axis, a third distal link movably coupled to said third distal joint, a fourth distal joint coupled to said third distal joint via said third distal link, said fourth distal joint having a fourth joint axis substantially perpendicular and intersecting to said third joint axis, a fourth distal link movably coupled to said fourth distal joint, a fifth distal joint coupled to said fourth distal joint via said fourth distal link, said fifth distal joint having a fifth joint axis substantially perpendicular and intersecting to said fourth joint axis, a fifth distal link movably coupled to said fifth distal joint, a sixth distal joint coupled to said fifth distal joint via said fifth distal link, said sixth distal joint having a sixth joint axis substantially perpendicular and non-intersecting to said fifth joint axis, said sixth distal joint movably coupled to said at least one end-effector element, a seventh distal joint coupled to said fifth distal joint via said fifth distal link, said seventh distal joint having a seventh joint axis substantially perpendicular and non-intersecting to said fifth joint axis, said seventh distal joint having a seventh joint axis substantially coincident to said sixth joint axis, said seventh distal joint movably coupled to said a second end-effector element, in such a way that said first and second end effector elements are movable relative to, and independently of, one another, a plurality of miniaturized driving cables, each coupling an actuation pulley at a proximal location of the support tube and another one of said joint driven pulley, placed on said slave distal joints; and In an embodiment, a coupling unit, placed at the proximal end of the support tube, mechanically connects the said master and said slave manipulators and their mechanical cable driven transmissions.

In an embodiment, an external manipulator mechanism, fixed relatively to the patient, is able to provide external degrees of freedom to the said support tube in such a way that the said slave unit can be inserted, positioned and moved within the abdominal cavity.

In an embodiment, said sixth distal joint has a sixth joint axis substantially parallel to said fifth distal joint axis, said sixth joint axis further coincident to said seventh joint axis.

In an embodiment, said sixth distal joint has a sixth joint axis substantially perpendicular and intersecting to said fifth distal joint axis, said sixth joint axis further coincident to said seventh joint axis.

In an embodiment, an eighth distal joint is provided between the said second distal joint and said third distal joint wherein said eighth distal joint has a eighth joint axis substantially perpendicular and intersecting to said second distal joint axis and third joint axis.

In an embodiment, the actuation pulleys of the master and slave manipulators are directly connected, in the said coupling unit, with multiple transmission ratios;

In an embodiment, the positioning mechanism further comprises a setup joint which connects the base to an operating room table or to the ground.

In an embodiment, the coupling unit is adapted to releasable connect the support tube to the master unit.

In an embodiment, an external positioning mechanism is provided which has external degrees of freedom of movement that are redundant with the degrees of freedom of movement of the said slave unit, comprises a remote centre of motion mechanism for pivoting the support tube about the incision point.

In an embodiment, said input commands may comprise the operator moving at least one master manipulator input linkage, wherein movement of said input handle corresponds to an analogous scaled increment movement of said slave end-effector.

In an embodiment, the forces experienced by the slave unit during a surgical procedure may be reproduced at the master input handle to provide the operator with force feedback.

In an embodiment, the slave articulate manipulator comprises a serial linkage having a number X of DOFs, and wherein said master input linkage is characterized by a number Y of DOFs where Y is equal to X.

In an embodiment, X comprises 7 slave degrees of freedom of movement and Y comprises 7 master degrees of freedom of movement.

In an embodiment, X comprises 8 slave degrees of freedom of movement and Y comprises 8 master degrees of freedom of movement, In an embodiment, the rigid support tube has a free internal channel, in which a third surgical instrument may pass, as well as a tool to exchange the gripper distal instruments;

In an embodiment, the third surgical instrument may be flexible, having a distal camera in the tip, or a gripping or a cutting or an ablating end-effector.

In an embodiment, the slave manipulator unit can pivot around the distal extremity of the guide tube by the said proximal shoulder component, being inserted aligned with the tube and then, when already inside the abdominal cavity, being externally actuated to turn into a working configuration, perpendicular to the said positioning tube's axis.

In an embodiment, the magnitude of movements of the slave manipulator unit can is scaled relatively to the movements of the said master manipulator unit.

In an embodiment, the slave articulated unit and said master articulated unit comprise:

a plurality of movable links; and a plurality of actuated joints, placed, between the said links, in a serial configuration; and a plurality of joint driven pulleys, placed on each said actuated joint, with the axis collinear with the axis of the respective joint, actuating the different degrees of freedom of the mechanism; and a plurality of actuation pulleys, remotely placed relatively to the movable links of the said articulated units and transmitting the actuation commands to the said driven pulleys by means of a cable driven mechanical transmission; and a cable driven mechanical transmission, composed by a plurality of driving cables, each coupling an actuation pulley at a proximal location of the mechanism and another one of said joint driven pulley, placed on said micro-mechanism distal joints, In an embodiment, each of the driving cable consist of a closed loop cable system, transmitting the actuation form the said actuation pulleys to the joint driven pulleys.

In an embodiment, the closed loop cable system may be composed by multiple sets of stages of closed loop cables, transmitting the actuation commands between them, form the said actuation pulleys to the joint driven pulleys, and keeping a constant total length for all the possible joint configuration of the said mechanism.

In an embodiment, the different closed loop cables of the multiple sets of stages of closed cable loops, transmit the actuation commands between them by a called idler tube, comprising an axisymmetric mechanical component, able to rotate around its axis, which is aligned with the axis of the said co-axial actuated joints.

In an embodiment, the closed loop cable Is composed by a single ended cable, whose both extremities are fixed in the said actuated pulley or in the respective said joint driven pulley or in a said idler tube.

In an embodiment, the closed loop cable is composed by a single endless cable, transmitting the controlled motion between said actuated pulleys, said joint driven pulleys and idler tubes by means of contact force*

In an embodiment, the closed loop cable is composed by two ended cables, whose extremities are fixed in both the said actuated pulley and the respective said joint driven pulley or in both the said actuated pulley and an idler tube or in both an idler tube and a said actuated pulley.

In an embodiment, the actuated joints can be of pivot type, where the axis of the said adjoining links are not alignment and the angle between them and changes with the movement of the said actuated joint, and co-axial type, where the axis of adjoining links are aligned or in a parallel configuration.

In an embodiment, the axis of the different idler tubes, for the different degrees of freedom and belonging to the same said co-axial joint, are collinear with the axis of the respective said co-axial joint.

In an embodiment, the axis of each said idler tube is keeps its collinear position by means of the contact with a set of external ball bearings or bushing components or any other component of the mechanism.

In an embodiment, the axial position of each said idler tube is kept, in relation to the other idler tubes of the same co-axial joint, by means of the contact between one or more parts of the idler tube, namely radial flanges or extremities, with external ball bearings or bushing components or any other component of the mechanism.

In an embodiment, the transmission of the actuated motion between the different stages of closed cable loops and the respective idler tubes is done through the force generated on the fixation of cable's extremities.

In an embodiment, the transmission of the actuated motion between the different stages of closed loop cables, for the same said closed loop cable system, and the respective said idler tubes is done through the contact force generated between them.

In an embodiment, the contact force may be increased by increasing the number of cable turns around the said idler tubes.

In an embodiment, the contact force may be increased by the use of a chain or flexible timing belt element or any other flexible transmission element in the close loop cable system.

In an embodiment, the chain or flexible element is a bead chain, comprising a closed loop cable containing some spherical or other axisymmetric elements, spaced by a constant pitch, along the segments of the cable that can be in contact with the said idler tubes.

DETAILED DESCRIPTION OF THE INVENTION

The present invention will be better understood from the following detailed description and with reference to the drawings which show:

Figure 5:
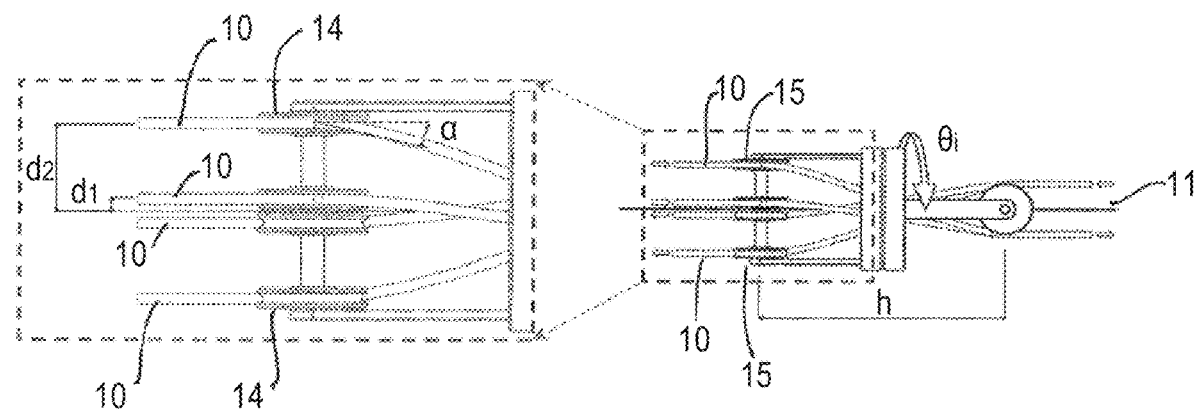
Figure 6:
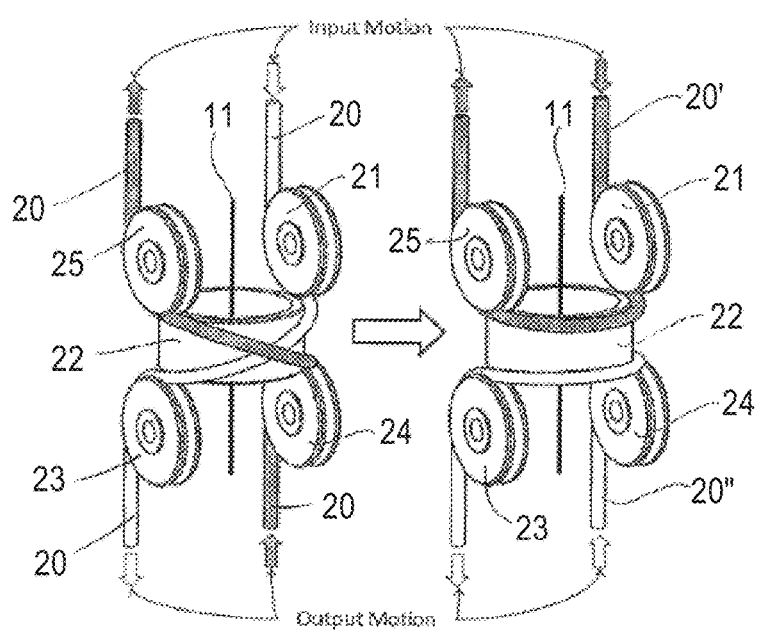
Figure 7:
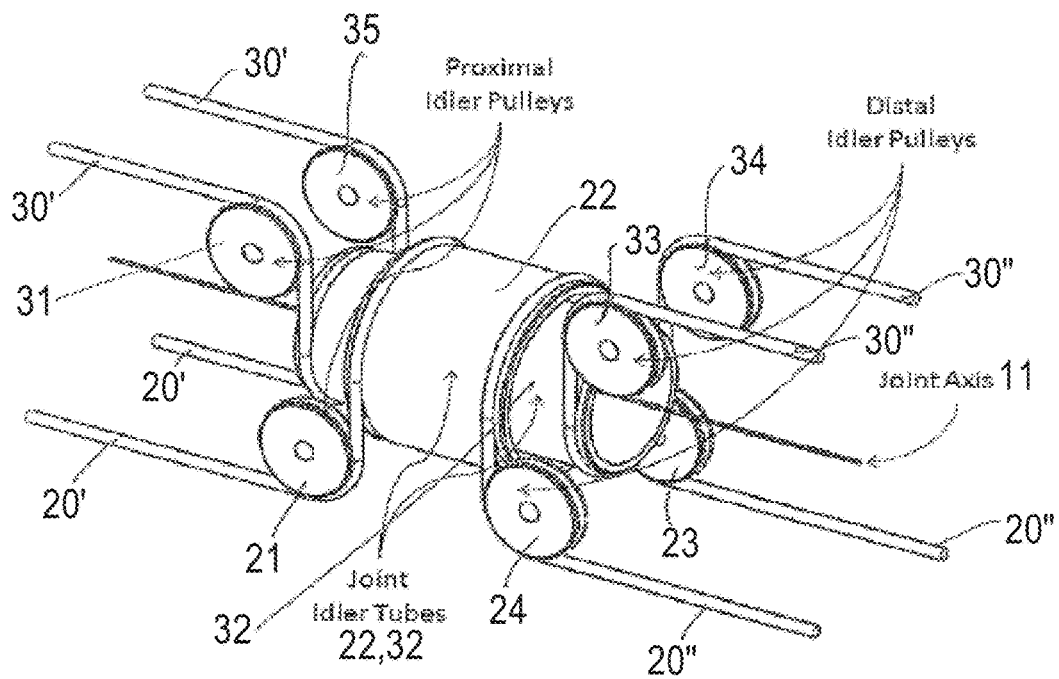
Figure 8:
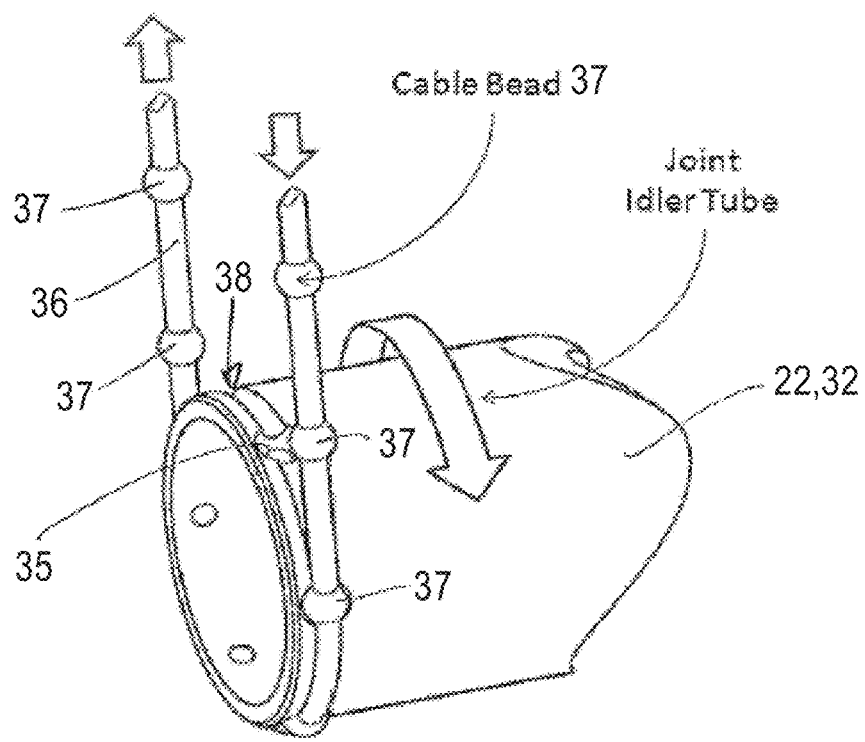
Figure 9:
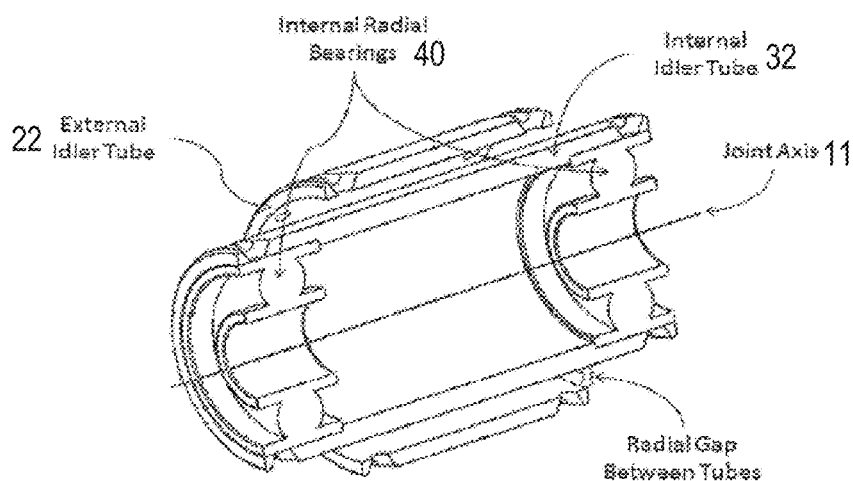
Figures 10A, 10B, 10C:
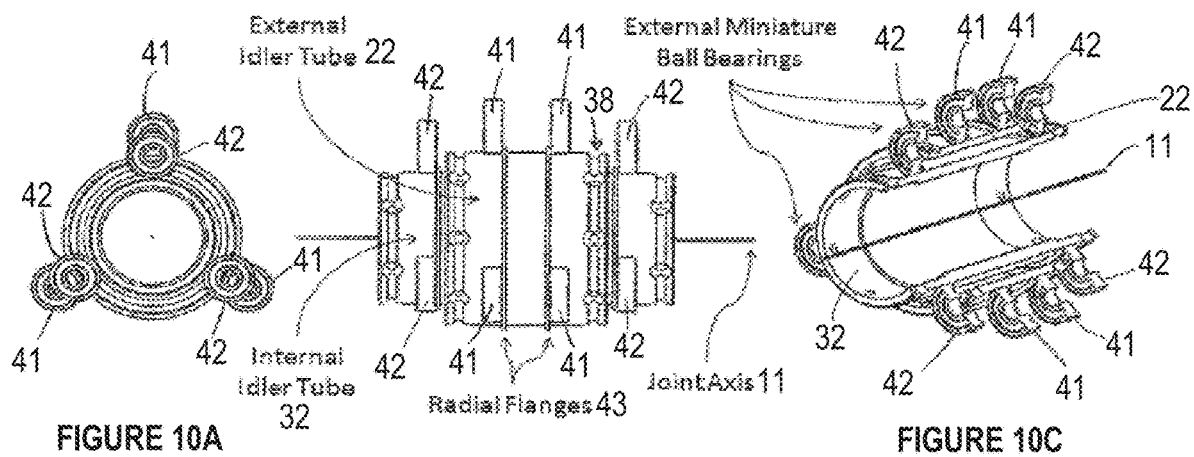
Figure 11:
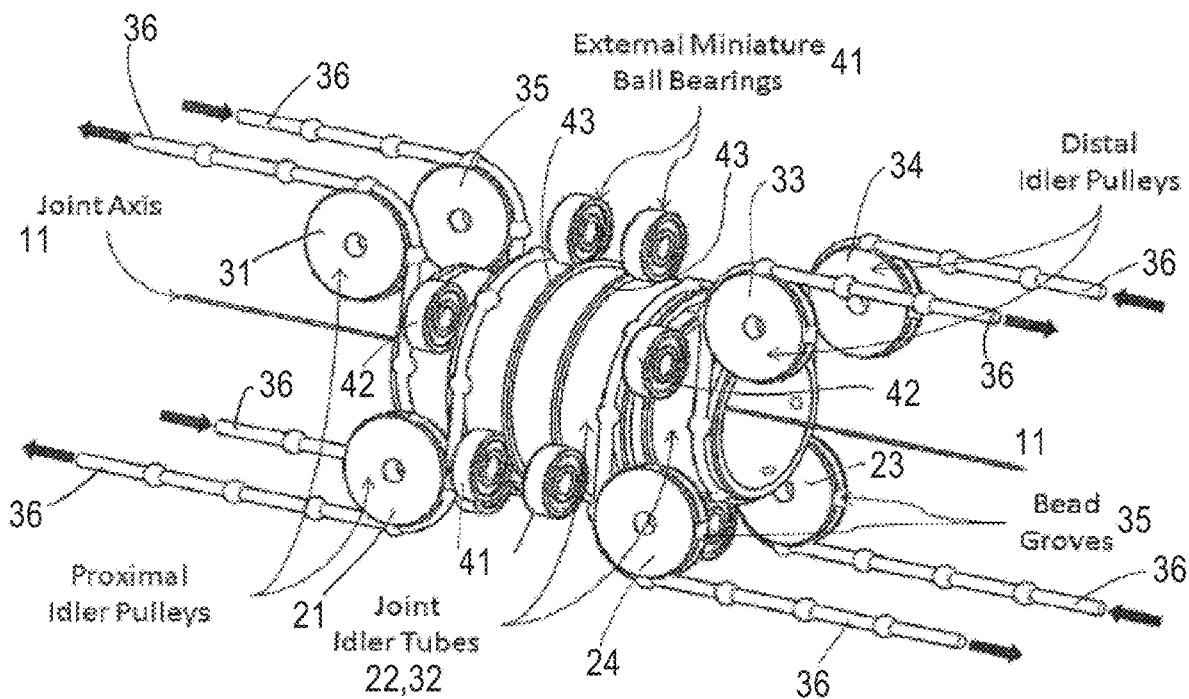
Figure 12:
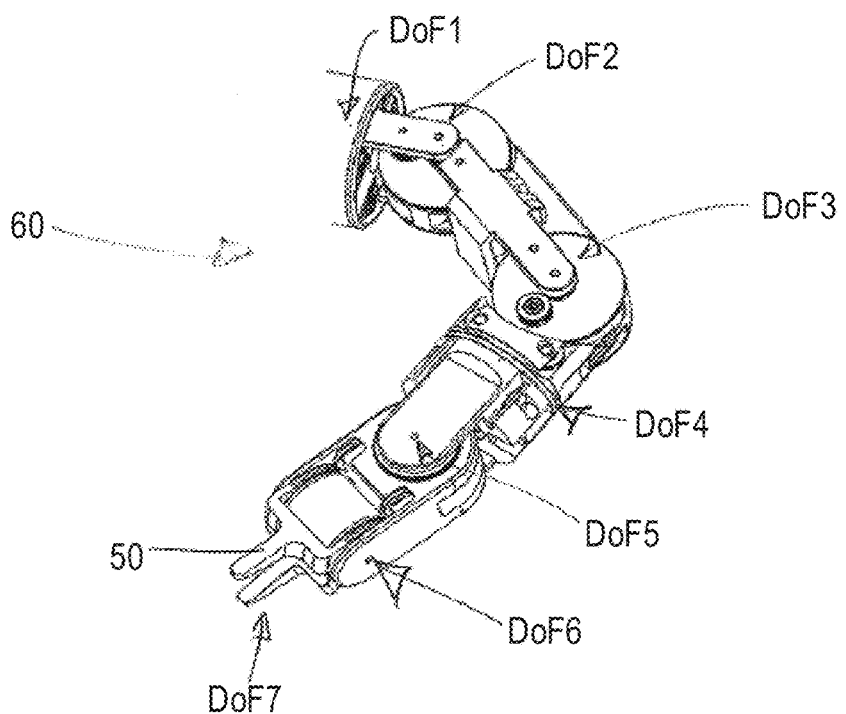
Figure 13:
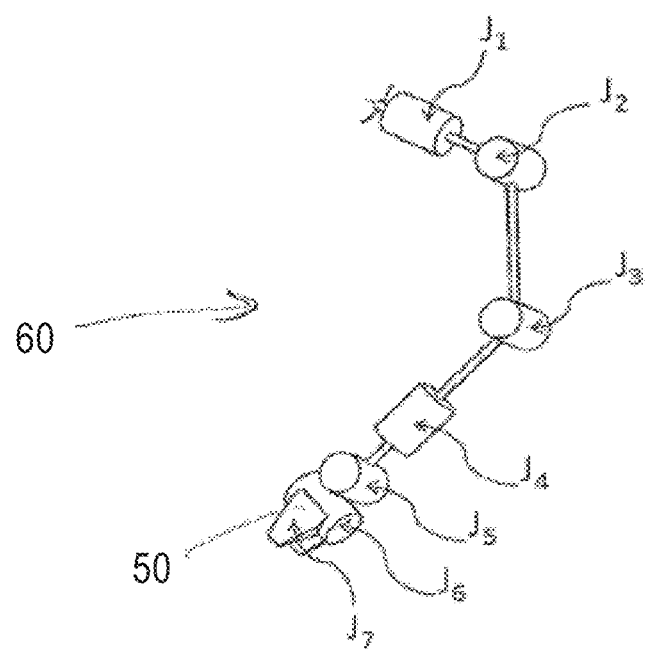
Figure 14:
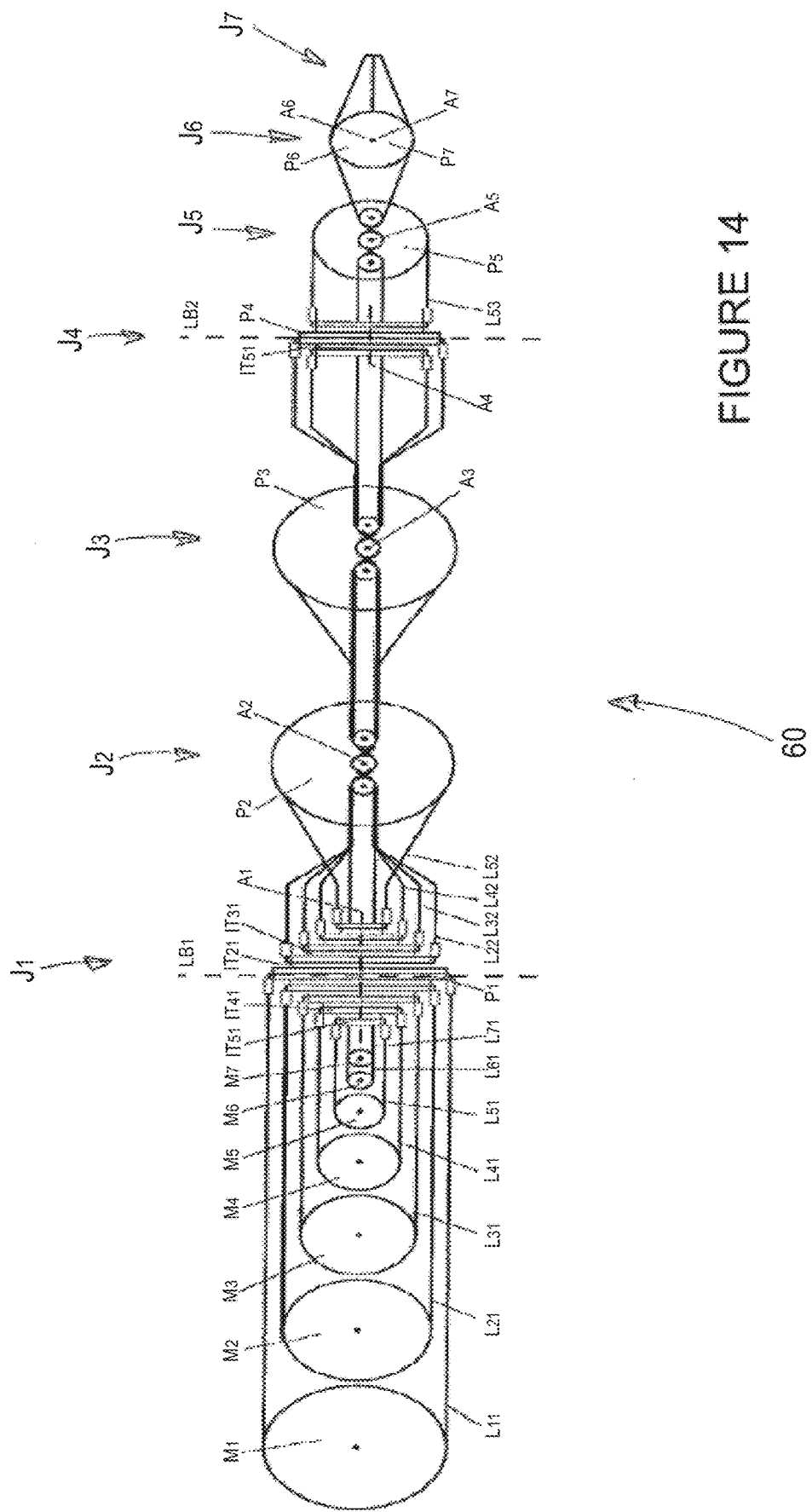
Figure 15:
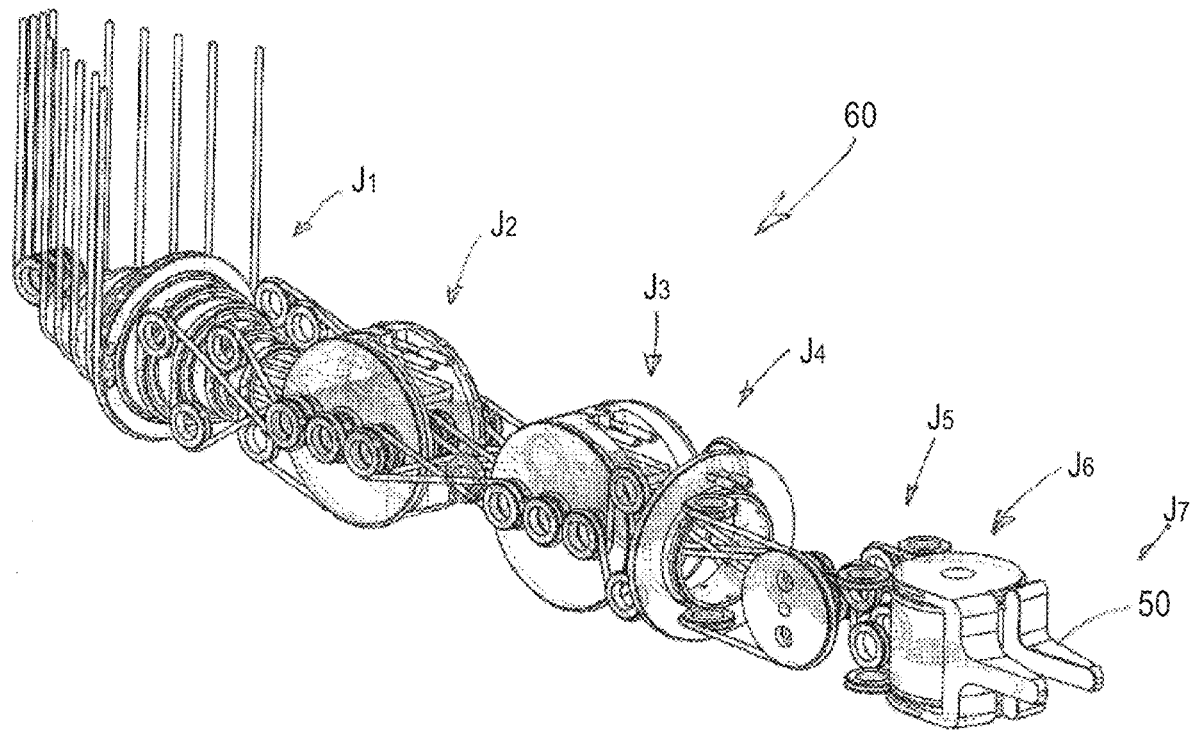
Figure 16:
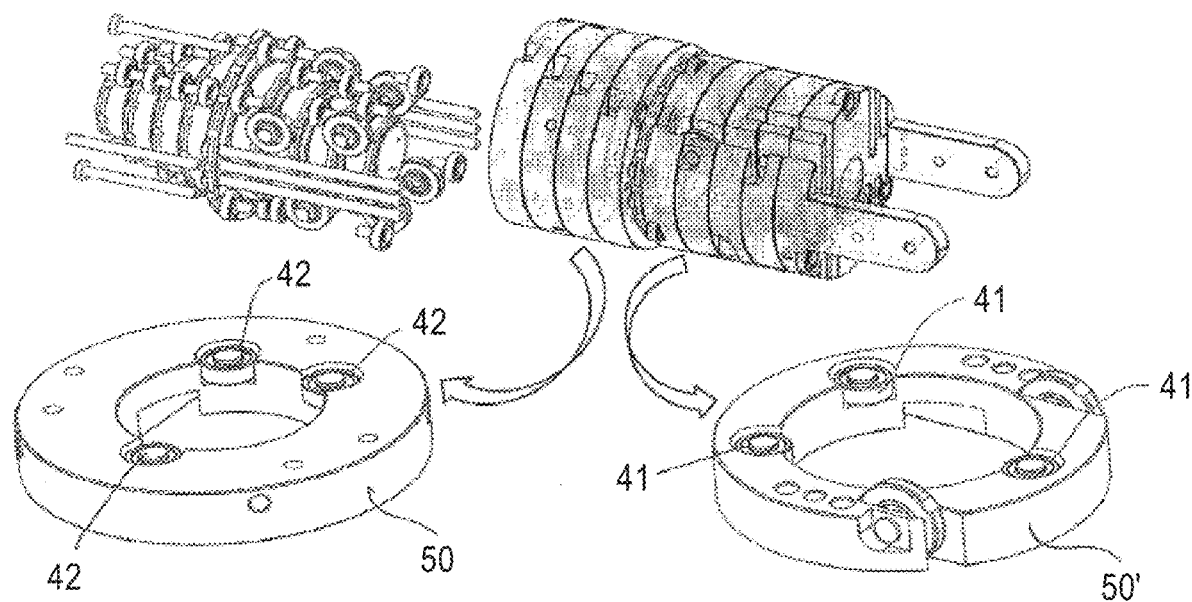
Figure 17:
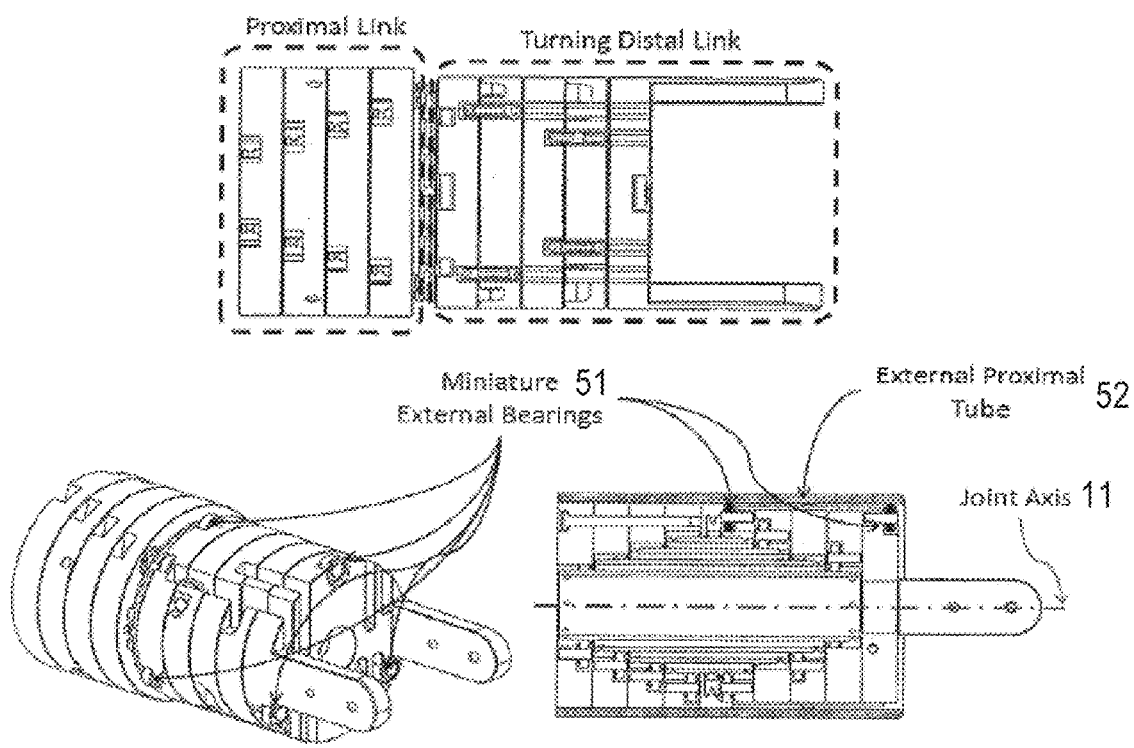
Figure 18:
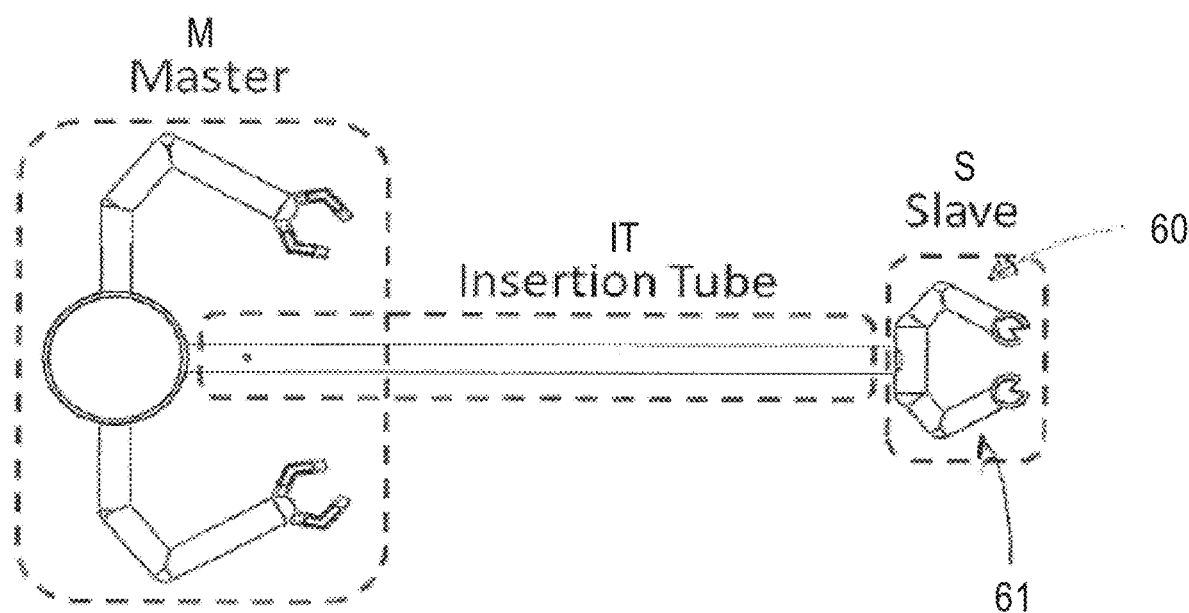
Figure 19:
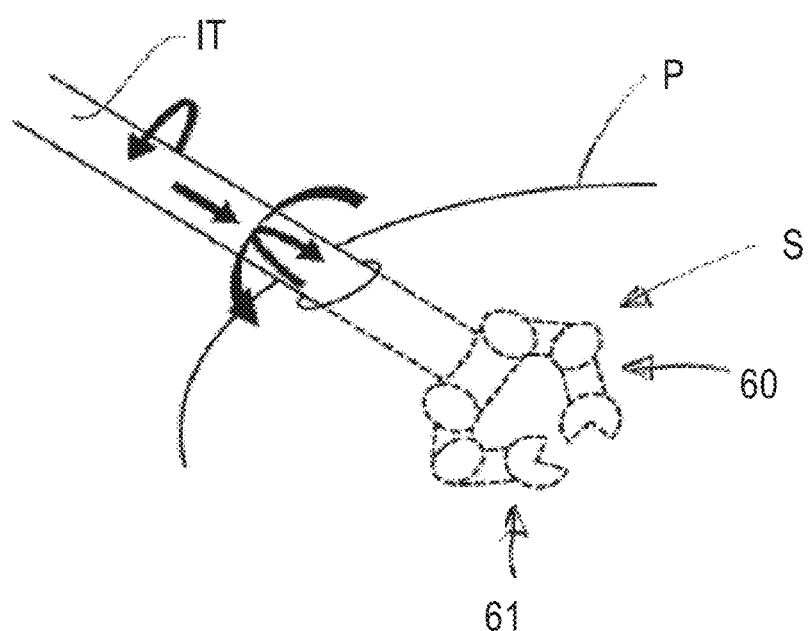
Figure 20:
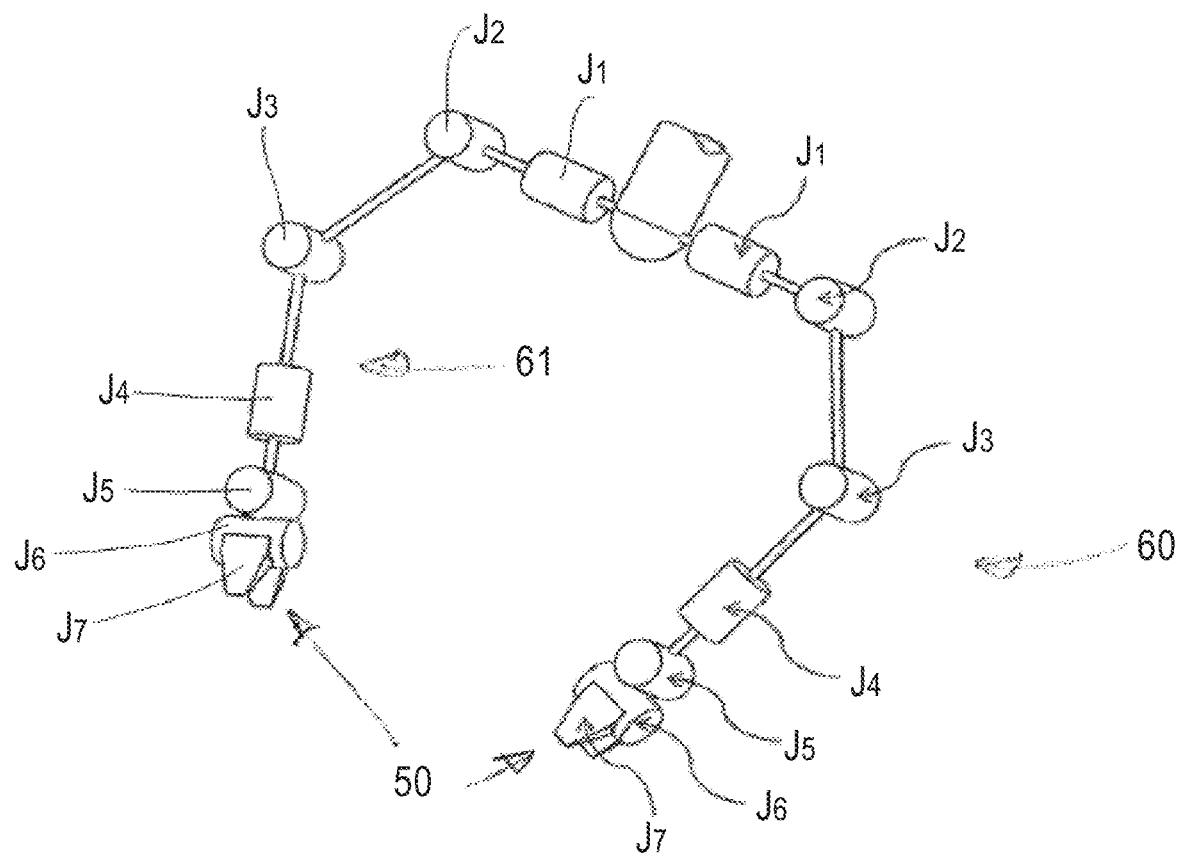
Figure 21:
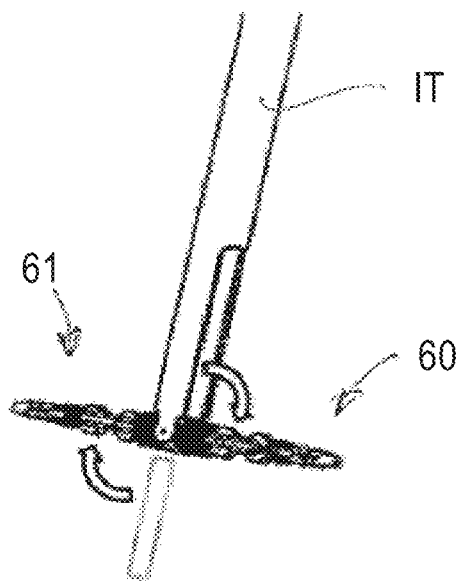
Figure 22:
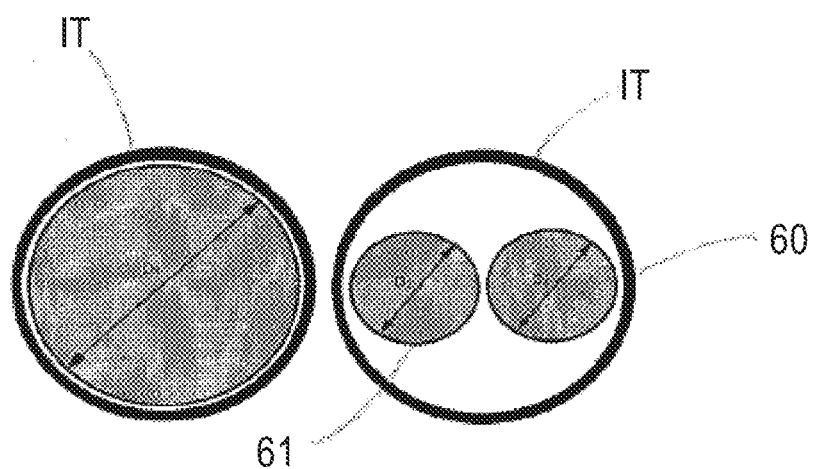
Figure 23:
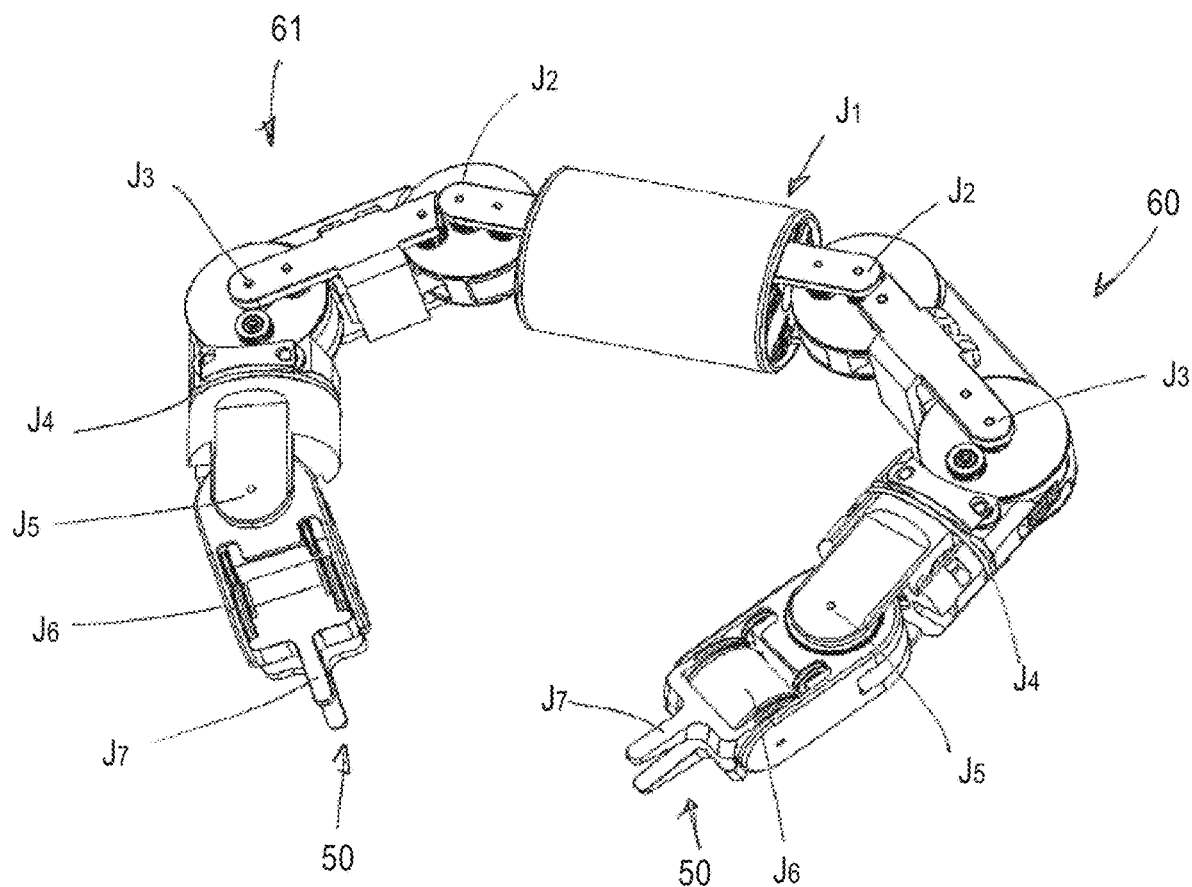
Figure 24:
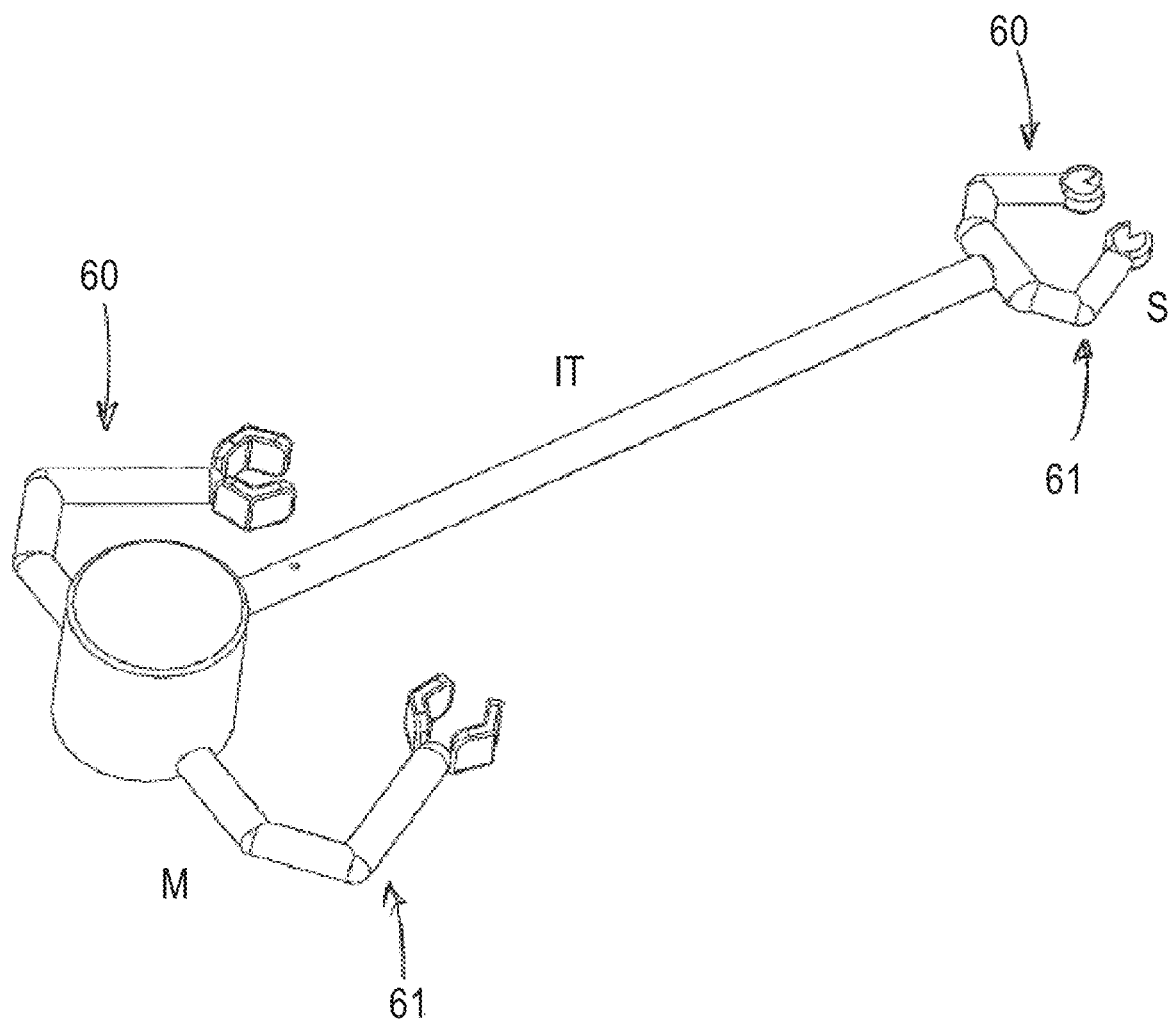
Figure 25:
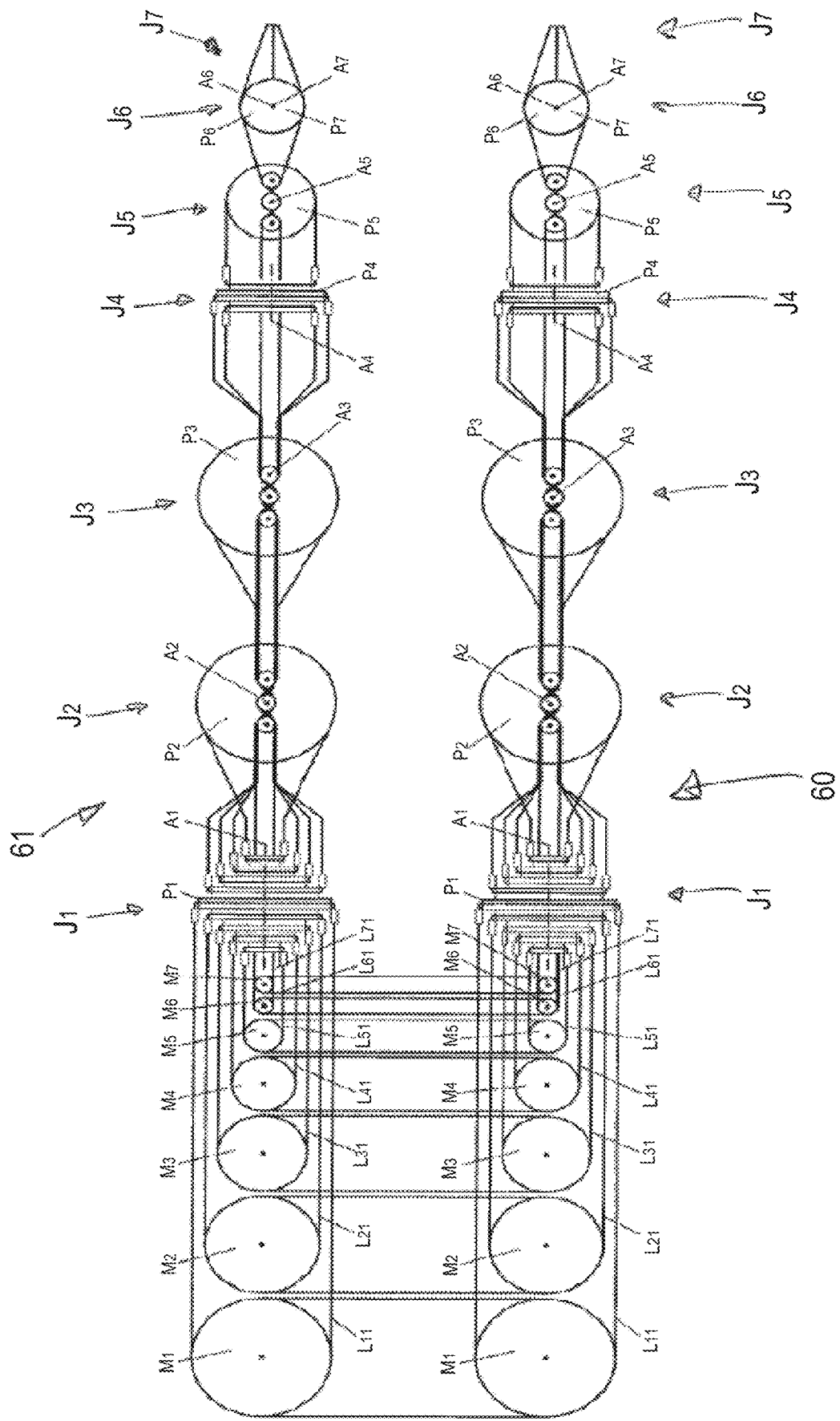
Figure 26:
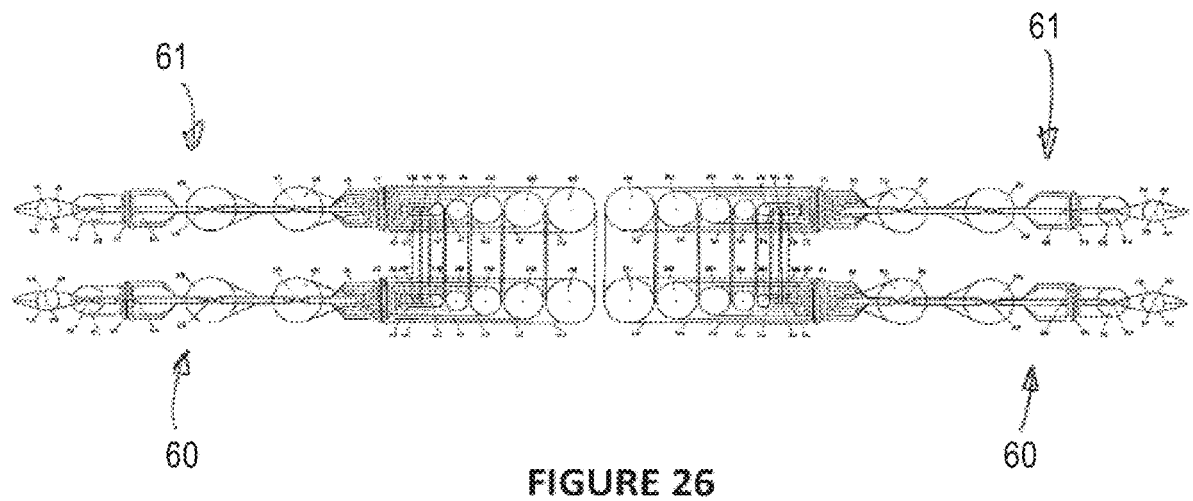
Figure 27:
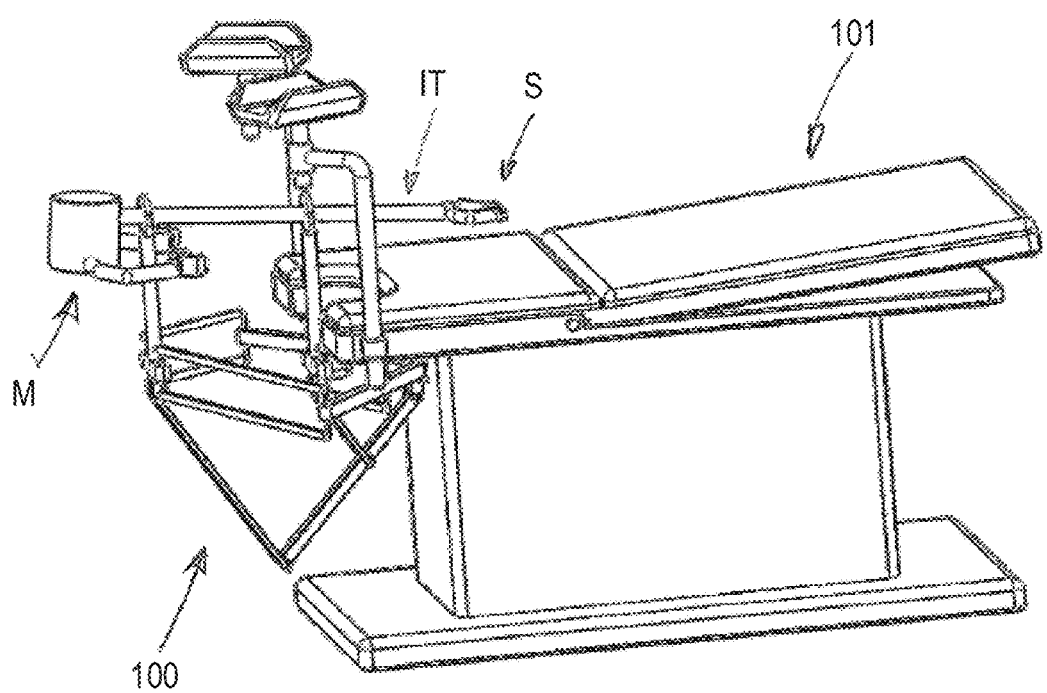

FIG. 5 further illustrates the problem of the cable routing along a co-axial joint;

FIG. 6 illustrates a Co-axial joint Concept Development;

FIG. 7 illustrates a Co-axial joint Concept, for a 2-DOF example;

FIG. 8 illustrates a bead chain turning the idler cylinder;

FIG. 9 illustrates a use of two ball bearings to mount an idler tube;

FIGS. 10A-10C illustrate a Radial and axial restriction of the joint idler tubes;

FIG. 11 illustrates a bead chain turning the idler cylinder;

FIG. 12 illustrates a 3D Model of a micro-manipulator according to the invention;

FIG. 13 illustrates a Kinematic Model of the micro-manipulator;

FIG. 14 illustrates cabling schematics of the 7-DOF micro-manipulator;

FIG. 15 illustrates 3D cable layout of the 7-DOF micro-manipulator;

FIG. 16 illustrates component mounting parts;

FIG. 17 illustrates radial and axial restriction of the joint turning distal link;

FIG. 18 illustrates the overall composition of a teleoperated mechanical system according to the invention;

FIG. 19 illustrates the external positioning degrees of freedom;

FIG. 20 illustrates the kinematic model of the micro-manipulators according to the present invention;

FIGS. 21 and 22 illustrate the insertion procedure for the micro-manipulators;

FIG. 23 illustrates a 3D Model of the endoscopic unit;

FIG. 24 illustrates an overview of the fully mechanical master-slave system;

FIG. 25 illustrates a cabling schematics of a sub-teleoperated system;

FIG. 26 illustrates a cabling schematic for the entire teleoperated system according to the present invention and FIG. 27 illustrates an overview of the entire teleoperated system with the external positioning mechanism.

In order to actuate the joints of a micro-manipulator for MIS, two basic approaches are possible;

(1) placing the actuators within the moving links of the manipulator, or integrating them in the joints directly, without transmission elements; or (2) placing the actuators on an external location, outside of the patient's body, having the motion transmitted to each joint by means of a complex mechanical transmission.

Internal actuation simplifies the mechanical configuration of the joint, reducing the complexity of the transmission chain. In particular, it has the great advantage that the motion of the joint is kinematically independent with respect to other joints. However, the size of the manipulator links is imposed by the dimension of the actuators and, due to technological power-to-volume limitations of available robotic actuation, it is quite difficult to obtain an anthropomorphic kinematics and the required working performances and dimensions required for an endoscopic system. Furthermore, the motors occupy a rather large space inside the robotic structure, making it difficult to host other elements, like different kind of sensors or internal structural components. Another issue is that, since the mass of the actuators is concentrated inside the manipulator links, the dynamic behaviour of the system and its response bandwidth are reduced.

A further negative aspect is related with the routing of both power and signal cables of the actuators, This issue is more serious for the actuation of distal joints than for the proximal ones, since the cables in distal joints produce a relatively large resistant torque and volume disturbance on the proximal joints.

As a consequence of all those above mentioned disadvantages, the internal actuation of these micro-manipulators was discarded in favour of a remotely actuated solution.

As opposite to internal actuation architectures, in remote actuation the joints are driven by actuators placed outside the moving links. It requires a motion transmission system, which must pass through the joints between the motor and the actuated joint and may bring problems of kinematic and dynamic coupling between the actuated joint and the previous ones, According to the type of adopted transmission elements, remote actuation systems can be classified as (1) flexible or (2) rigid transmission. This last way of transmission is mainly based on articulated linkages or rolling conjugated profiles (e.g. gear trains) and although may guarantee an increased stiffness of the systems, its implementation in miniature and complex multi-DOF mechanisms is extremely difficult.

On the other hand, flexible transmissions are based on deformable connections that can adapt to variations of configuration by changing the transmission path. They are based on flexible elements with translating motion, subject to tension (more frequently) or tension and compression. Two further subcategories can be identified: pulley-routed flexible elements (tendons, chains, belts) or sheath-routed flexible elements.

In this case, since it was aimed to develop a teleoperated mechanism with good force reflection properties, enabling bilateral force reflection, it was decided to use pulley-routed flexible elements, cables, with bail bearing mounted pulleys, in order to reduce the amount of friction losses along the mechanical transmission.

Figure 1:
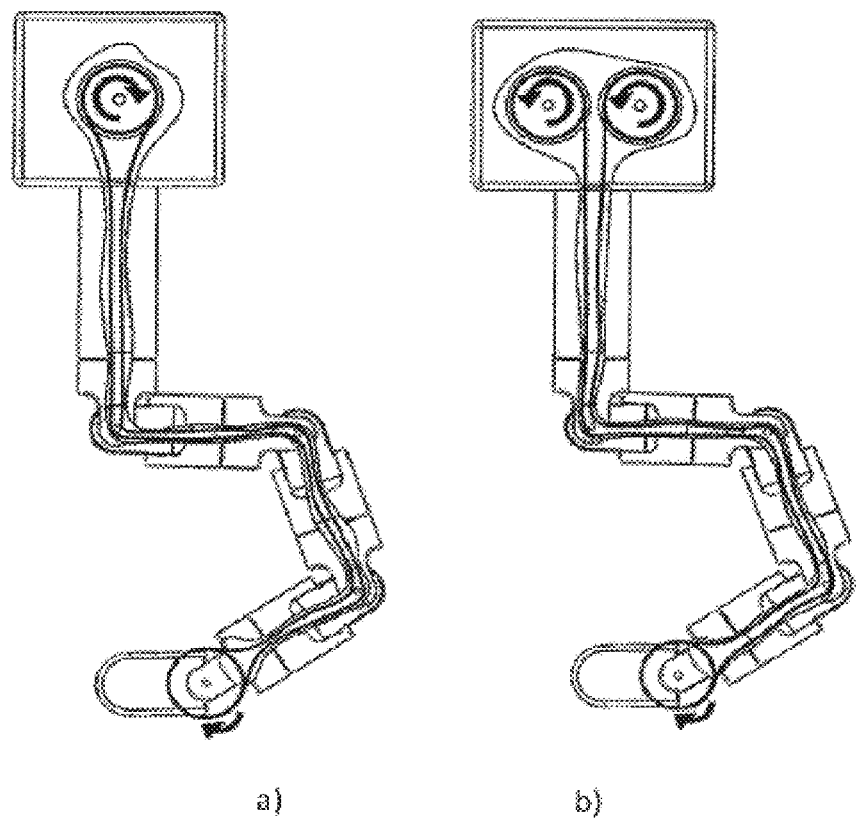
FIG. 1 illustrates two different architectures for remote actuated cable driven systems, a) One actuated pulley per DOF b) Two actuated pulleys per DOF.

Remote cable driven actuation can be applied according to different types of organization, depending on the number of actuated pulleys used per joint. In particular, it is possible to recognize two main actuation architectures:

(1) two actuated pulleys per DOF—each one can generate a controlled motion in one direction only and the return motion in the opposite direction must be obtained by an external action, which can be a passive (e.g., a spring) or an active system (e.g., an antagonistic actuator); this is the case of tendon-based transmission systems;

(2) one actuated pulley per DOF—each one can generate a controlled motion in both directions and can be used alone to drive the joint. These two architectures are illustrated in FIG. 1(a) (one actuated pulley per DOF) and (b) (two actuated pulley per DOF).

Since the second solution requires a higher number of components and brings additional complexity and cost to the mechanical system, the chosen architecture was the one that uses a single actuated pulley per DOF. In this case, the achievable performances are similar in both directions, but particular attention must be paid to backlash. Usually, it is necessary to preload the transmission system. Furthermore, the adoption of a closed loop tendon transmission requires that the overall length of the tendon route must be kept constant, for all the possible configurations of the manipulator.

$$\Delta l = 0, \forall q \in W_q$$

In spite of this additional complexity, this actuation scheme has been used, for simple applications, with only a few DOF or low dexterity. However, in a multi-DOF configuration, with high dexterity, reduced dimensions and high payload requirements, several non solved problems arrive from the implementation of this kind of actuation transmission.

Figure 2:
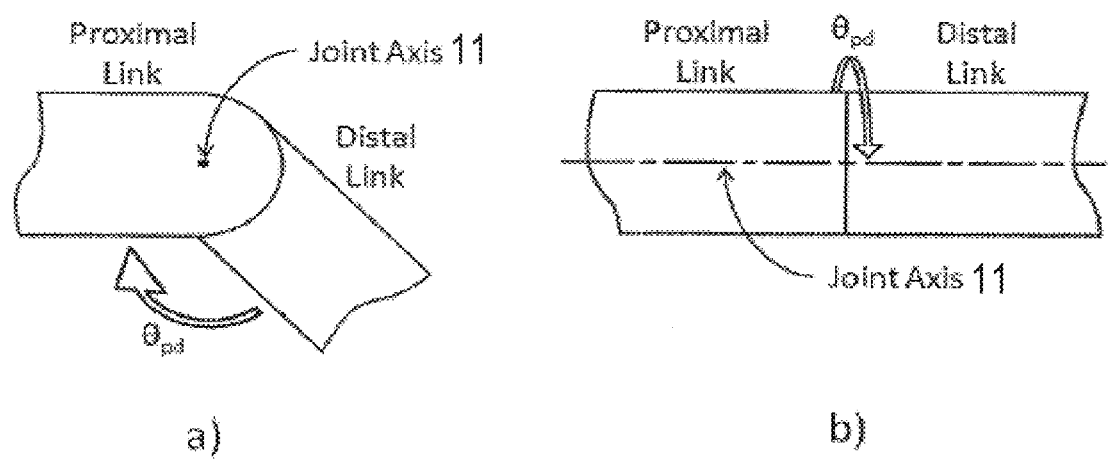
FIG. 2 illustrates (a) a Pivot Joint and (b) a Co-axial Joint.

In the required kinematic design of high dexterity endoscopic micro-manipulators, two joint configurations may be present, which can be classified as (1) pivot joints or (2) co-axial joints, both being illustrated in FIGS. 2(a) and (b). The distinction is related to the relative alignment of adjoining links. While in the first kind, the angle, $\theta_{pd}$, between the proximal, p, and distal, d, links changes with the movement of the joint, see FIG. 2 *a*), in the co-axial configuration the proximal joint has an axial rotation movement in relation to the distal one, see FIG. 2 *b*).

Figure 3:
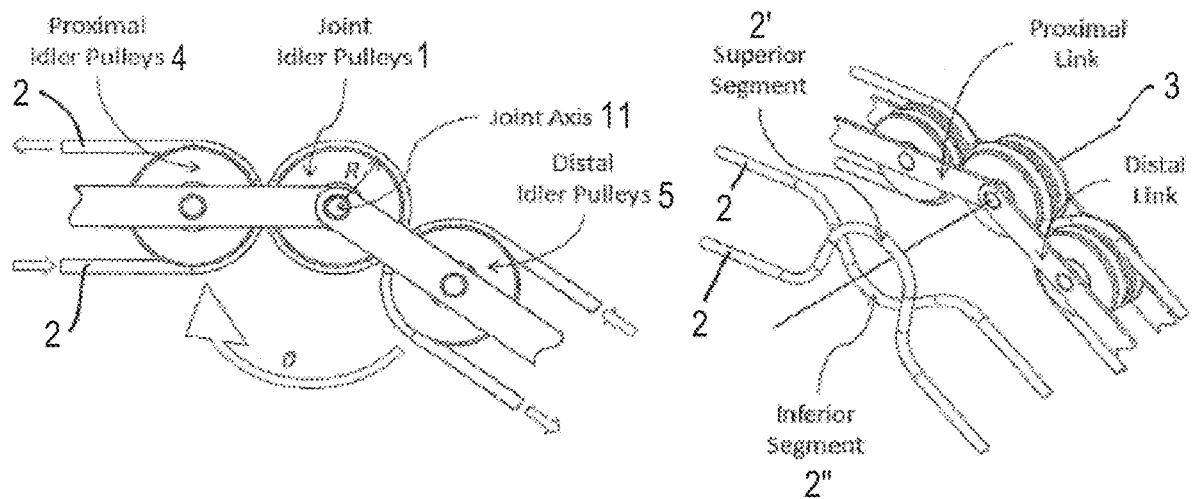
FIG. 3 illustrates a cable rooting along a Pivot Joint, (a) being a 2D view and (b) being a perspective 3D view.

The cable routing method utilized for pivot joints is relatively standard and can be seen in several already developed solutions. As illustrated in FIG. 3, for this kind of configurations, the cable 2 is wrapped around a pulley 1, called the "joint idler pulley," which is concentric with the axis of revolution 3 of the joint. To maintain a constant cable length, the cable 2 must remain in contact with the joint idler pulley 1 at all times. In this way, if the joint turns an angle D on the anticlockwise direction, the length of the superior segment 2', in contact with the idler pulley, will increase and the inferior segment 2" will decrease, by the same value, RD, guaranteeing the constant length of the cable closed loop. As said before, each DOF is actuated by two cables, wrapped around a set of two pulleys 1, passing through the joint. The multi-DOF case, with n DOF, would require a stack of 2n pulleys.

As illustrated in FIG. 3, the joint in addition comprises a set of proximal idler pulleys 4 and a set of distal idler pulleys 5 which guide the cable 2.

Figure 4:
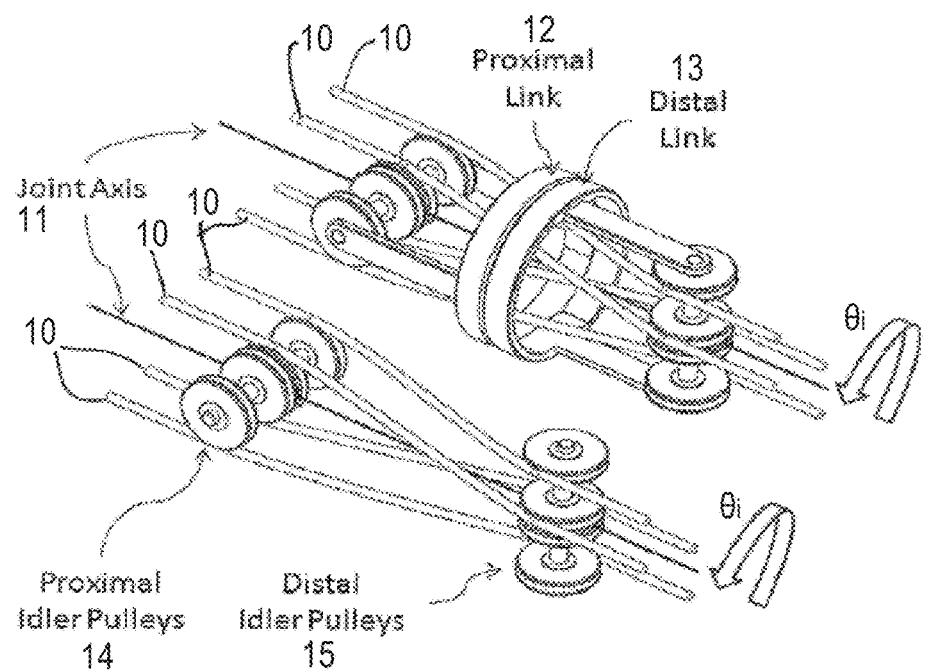
FIG. 4 illustrates the problem of the cable routing along a co-axial joint.

However, for the co-axial joints, the cable routing is much more complex. Some solutions to avoid this problem have already been proposed but, to the best of the inventor's knowledge, not for such a small dimension multi-DOF system with such a high dexterity and payload requirements. The problem consists in having an array of cables 10 being twisted about a co-axial axis 11, as shown in FIG. 4, when the proximal link 12 and the distal link 13 rotate relatively, with the two 10 cables actuating the same joint being stretched in the same way, thereby increasing the total length of the closed loop. FIG. 4 also illustrates the proximal idler pulleys 14 and the distal Idler pulleys 15.

This stretch of the different closed loops of cable 10 generates a resistant rotation moment that might be critical for multi-DOF systems. Another source of problems, as seen in FIG. 5, is the misalignment of the cables 10 in relation to the idler pulleys 14, identified by the angle α caused by this twist, which may cause the disengagement of the cables from the pulleys 14 and the rubbing of the cables 10, generating friction and wear. These problems are especially critical on the proximal joints of the manipulators, due to the high density of cables that actuate the distal joints.

In some applications of micro cable driven manipulators for MIS (minimally invasive surgery), this difficulty is minimised due to the low complexity (low number of internal DOF) of the system and the large ratio between the length of the instrument shaft, h, and the distance between the joint axis and the cables, d. In this way, the misalignment of the cables in relation to the idle pulleys is almost negligible and the change in length of the cables is small, generating a very small resistant rotation moment. In the present case however, due to the high number of internal DOF and the anthropomorphic kinematic configuration, this solution may not be applied.

The developed solution for the present invention is based on the concept shown in FIG. 3, which is adapted to be suitable for co-axial joints. More specifically, the configuration is similar but the two set of proximal and distal idler pulleys are separated by a joint idler pulley to allow the cables, belonging to the same closed loop, to be wrapped around the joint idler pulley, which is now in a perpendicular configuration (rather than a parallel one as illustrated in the embodiment of FIG. 3), aligned with the axis of the joint.

This configuration according to the present invention is illustrated in FIG. 6. In this configuration, the crossing and rubbing of the two cables is evident (see the drawing on the left in FIG. 6) and the way to avoid it resides in dividing the single primitive closed loop in two (as illustrated in the drawing on the right in FIG. 6). By doing this, the single closed loop is divided in two new closed loops, whose relative motion is now transmitted through an axial idler pulley (or tube) see FIG. 6.

More specifically, FIG. 6 shows (on the left side drawing) a first intermediate configuration derived from FIG. 3. In this first intermediate configuration, the cable 20 passes a first proximal idler pulley 21, then over the joint idler pulley 22 (or joint idler tube), a first distal idler pulley 23, goes to the tool to be controlled and comes back to a second distal idler pulley 24, crosses over the joint idler pulley 22 and finally passes a second proximal idler pulley 25. As one can easily see on the drawing of the right side of FIG. 6, the cable 20 crosses over the joint idler pulley 22 which renders this configuration unsuitable for the intended applications. To overcome this problem, the solution is illustrated in the drawing on the left side of FIG. 6. Specifically, in this configuration, the cable 20 is divided into two loops 20' and 20" which are separated.

The first loop 20' passes the first idler pulley 21 the over the joint idler pulley and back over the second proximal idler pulley 25. The second loop 20" passes the second distal idler pulley 24, then over the joint idler pulley 22 and then over the first idler pulley 23. Accordingly, the motion of the first cable loop 20' may be then transmitted to the second cable loop 20" via the joint idler pulley 22.

As an extension of this concept, to be able to form a multi-DOF system, the joint according to the present invention will be composed by several co-axial idler tubes/pulleys corresponding to the pulley 22 of FIG. 6, with different lengths and different diameters, allowing the hosting of the different sets of proximal and distal idler pulleys for the different closed loops actuating the different joints. FIG. 7 illustrates the basic principle of this extension. For example, one sees in the figure the system as illustrated in FIG. 6 (drawing on the right side) and described above (cables 20', 20", pulleys 21, 23, 24 and joint idler tube 22) and there is accordingly a second similar system for the second DOF. Specifically, basically the second system is similar to the first one with two cable loops 30', 30", proximal idler pulleys 31, 35, distal idler pulleys 33, 34 and a joint idler tube/pulley 32. This pulley 32 has a smaller diameter than the pulley 22 and is concentrical with this pulley 22, aligned along the same axis 11 (the joint axis).

Accordingly, this allows to have two independent actuating systems in the same joint, and the principle may be extended further in order to add additional DOF, the principle being to add the concentrical joint idler tubes/pulleys.

Systems with several stages of endless cables have been used in several mechanical systems where, in order to ensure enough friction to transmit the motion between consecutive closed loops, timing belts have been frequently used. However, for this specific solution, they are not a suitable choice. The main problem is related to the fact that, although timing belts might be used in out-of-plane configurations, in this reduced dimensions application, since the out-of-plane idler pulleys are too close to each other, this kind of configurations are not feasible.

A standard cable could be a solution. However, the friction generated by the cable in contact with the idle pulley and/or tube, for any pair of materials, wouldn't be sufficient and the wear would be excessive. The cable could also be wrapped several times around it, with an exponentially increased friction, but it would promote an unacceptable axial movement of the idler pulley.

Since in this configuration the motion transmission can only be made through half a turn of contact of cable around the joint idler tube/pulley, the friction in the contact is maximized by a specially developed bead chain, which is illustrated in FIG. 8. It is composed by a continuous stiff rope 36 (corresponding to the cables 20', 20", 30', 30" described above) with several spherical beads 37, placed with constant pitch, in the segments of the cable that may be in contact with the joint idler tube 22, 32 as described with reference to FIGS. 6 and 7 above, The bending flexibility, axial symmetry, strength and compactness of this bead chain make it suitable for this application, where high load resistance, no slipping, low volume and right-angle driving are major requirements.

Wire ropes or cables are available in a variety of strengths, constructions, and coatings. Although cable strength generally increases with diameter, the effective minimum bend radius is decreased. Cable compliance, cost, and construction stretch generally increases with strand count.

During operation, the cable runs in a grooved surface 38, placed on the extremities of the idler tubes 22, 32 and the beads seat in sprocket indentations 39, where the shear force is generated.

As was already explained in the previous section, in a multi-DOF configuration, the primitive closed loop is divided in two new closed loops, whose motion in transmitted through the axial idler tube 22, 32, which should be able to rotate independently from other concentrical idler tubes/pulleys which are present in accordance with the embodiment illustrated in FIG. 7, while keeping its fixed axial position. This could be achieved for example by the use of two internal radial ball bearings 40, in a standard configuration, as shown in FIG. 9 where the joint idler tubes/pulleys 22, 32 correspond to the one described above.

However, in a multi-DOF system, the space gap between the concentric joint idler tubes 22, 32 is not enough to place two ball bearings for each idler tube and so, several (for example preferably six) miniature external ball bearings may be used to guarantee the concentricity of each idler tube. Specifically, one uses six external bearings per joint idler tube/pulley 22, 32 to ensure a correct and stable positioning. The axial movement is constrained by the contact of two radial flanges with the six bearings as illustrated in FIGS. 10A-10C.

More specifically, FIG. 10A illustrates an axial view of the arrangement of bearings 41, 42 on the joint idler tube/pulley 22, 32. FIG. 10B illustrates a front view of the joint arrangement with the bearings 41, 42 and flanges 43 used to block the lateral motion of the bearings. FIG. 10C illustrates a cut and perspective view of the joint arrangement as described.

For an application example with two transmitted degrees of freedom, the layout of the joint using the principles of the present invention described above will look like the one shown in FIG. 11. More specifically, this embodiment corresponds to the one illustrated in FIG. 7, using the cable 36 with beads 37 and the joint idler tube 22, 32 of FIG. 8 with the grooved surface 38, placed on the extremities of the idler tube 22, 32 and the beads seat in sprocket indentations 39. Accordingly, numerical references used in said previous figures apply here to corresponding elements as well as the description.

Making use of the transmission concept previously proposed, the design of several novel mechanical surgical instruments can be implemented. The main goals of these platforms are:

(1) to provide high dexterity within the abdominal cavity,
(2) to provide enough precision and stiffness, enabling the performance of accurate surgical procedures,
(3) to have reduced dimensions and
(4) to have low inertia and friction, allowing good force reflecting properties, increasing the transparency of the teleoperated mechanical system.

As an example of application, FIG. 12 shows the overall composition of a mechanical system such as a manipulator, which is able to provide the desired dexterity to the performance of complicated surgical procedures, like pulling and cutting tissue or eventually suturing. This manipulator has high dexterity, high payload capacity, stiffness and precision, with seven degrees of freedom (six to orientate and to move the distal gripper, i.e. DOF1 to DOF6, and one degree of freedom, DOF7, to actuate the gripper 50). In order to be as intuitive to control as possible, the degrees of freedom are designed with an anthropomorphic kinematics, resembling a simplified human arm.

Achieving a kinematic model that matches the one of the human arm is a challenging task, especially in cable-driven devices, where the cables must be routed through joint axes while maintaining constant cable length.

Anthropomorphic joint approximations can be modelled at varying degrees of accuracy and complexity. The level of complexity needed for a suitable representation depends highly on the desired tasks to be performed. For this specific system, since it is aimed to control the position and orientation of the end-effector in the 3D space, the movement of each anthropomorphic micro-manipulator is achieved through the articulation of six single-axis revolute joints plus the gripper 50 actuation.

The manipulator degrees of freedom are labelled from J1 to J7 (as DOF1 to DOF7 illustrated in FIG. 12), from the proximal to the distal joint, in the order shown in FIG. 13.

The shoulder abduction-adduction and flexion-extension are then modelled as a composition of two intersecting axes, $J_1$ and $J_2$. The elbow flexion-extension is modelled by a single axis parallel to the second shoulder axis, $J_3$. Forearm prono-supination takes place between the elbow and wrist joints as it does in the physiological mechanism, $J_4$, while two orthogonal joints, $J_5$ and $J_6$, represent the wrist flexion-extension and radial-ulnar deviation. The offset between $J_5$ and $J_6$ is due to the physical limitation of having two cable actuated joints with intersecting axis. Finally, the gripper actuation is represented by $J_7$ and is a result of the actuation of both gripper blades about the same axis.

The resultant kinematics is identical to the Elbow Manipulator, which is considered to be the optimal kinematics for a general 6-DOF revolute joint manipulator.

As illustrated in FIG. 13, joints $J_1$ and $J_4$ are modelled as co-axial joints, and joints $J_2$, $J_3$, $J_5$, $J_6$ and $J_7$ are pivot joints.

The cabling topology of the entire manipulator using the principle of the present invention is schematically shown in FIG. 14 which uses the above description of configurations of pivot joints and co-axial joints according to the present invention. The design of the mechanism is such that the closed cable loop systems which control each degree of freedom are moved by the same actuated driven pulley placed in the external part of the body.

Pulleys $M_1$-$M_7$ actuate joints $J_1$-$J_7$ through a set of cable loops, $L_1$-$L_7$, that, depending of the degree of freedom, can have one, two or three stages, separated by the loop break lines, $LB_1$ and $LB_2$. A single cable loop runs about multiple idler pulleys, which are placed in proximal and distal positions from the driven pulleys and joint idler tubes.

Since each idler pulley is mounted on a ball bearing, in all the closed loops, with the exception of $L_6$ and $L_7$, the cables are perfectly aligned with the idler pulleys, idler tubes and driven pulleys. In this way, the idler pulleys don't suffer any torque, which cause them to tilt about an axis orthogonal to the pulley shaft. Since the single pulley bearings are not designed to handle moments, tilting the pulley forces it to rub on its neighboring pulley, creating additional friction. Also, the bearings themselves are not meant to run tilted, which can create even more friction.

Cable loop $L_1$ is composed by a single loop stage, $L_{11}$. Starting from the actuated pulley $M_1$, $L_{11}$ engages directly the driven pulley $P_1$, passing by two proximal idler pulleys of joint $J_1$, and returns back to $M_1$, where both terminations are fixed.

Cable loop $L_2$ is composed by two loop stages, $L_{21}$ and $L_{22}$. Starting from the actuated pulley $M_2$, $L_{21}$ engages the idler tube (i.e. the joint idler tube/pulley defined above) $IT_{21}$, passing by two proximal idler pulleys of $J_1$, and returns back to $M_2$, where both terminations are fixed. From $IT_{21}$, $L_{22}$ passes by two distal idler pulleys of $J_1$ and engages the driven pulley $P_2$, where both terminations are fixed.

Cable loop $L_3$ is composed by two loop stages, $L_{31}$ and $L_{32}$. Starting from the actuated pulley $M_3$, $L_{31}$ engages the idler tube (i.e. the joint idler tube/pulley defined above) $IT_{31}$, passing by two proximal idler pulleys of $J_1$, and returns back to $M_3$, where both terminations are fixed. From $IT_{31}$, $L_{32}$ passes by the two distal idler pulleys of $J_1$, by the idler pulleys (proximal, joint and distal) of $J_2$ and engages the driven pulley $P_3$, where both terminations are fixed.

Cable loop $L_4$ is composed by two loop stages, $L_{41}$ and $L_{42}$. Starting from the actuated pulley $M_4$, $L_{41}$ engages the idler tube (i.e. the joint idler tube/pulley defined above) $IT_{41}$, passing by two proximal idler pulleys of $J_1$, and returns back to $M_4$, where both terminations are fixed. From $IT_{41}$, $L_{42}$ passes by the two distal idler pulleys of $J_1$, by the idler pulleys (proximal, joint and distal) of $J_2$ and $J_3$ and engages the driven pulley $P_4$, where both terminations are fixed.

Cable loop $L_5$ is composed by three loop stages, $L_{51}$, $L_{52}$ and $L_{53}$. Starting from the actuated pulley $M_5$, $L_{51}$ engages the idler tube (i.e. the joint idler tube/pulley defined above) $IT_{51}$, passing by the two proximal idler pulleys of $J_1$, and returns back to $M_5$, where both terminations are fixed. From idler tube $IT_{51}$, $L_{52}$, which is an endless closed loop cable stage, passes by the two distal idler pulleys of $J_1$, by the idler pulleys (proximal, joint and distal) of $J_2$ and $J_3$ and engages the idler tube $IT_{52}$. From idler tube $IT_{52}$, $L_{53}$ passes by the two distal idler pulleys of $J_4$ and engages the driven pulley $P_5$, where both terminations are fixed.

For each one of the degrees of freedom $J_6$ and $J_7$, the cable loops $L_6$ and $L_7$ have a single stage, $L_{61}$ and $L_{71}$. They run from the actuated pulleys $M_6$ and $M_7$ until the distal driven pulleys, $P_6$ and $P_7$, passing through the idler pulleys of all the proximal pivot joints of the micro-manipulator. On the other hand, when passing by the co-axial joints $J_1$ and $J_4$, they are not passing through idler pulleys and are twisted around the joint axis. However, due to extensive length of the loops, between the actuated and driven pulleys, and the short distance between the cables and the axis of rotation, the resulting stretch of the cables is slight, so that the resulting resistance to rotational motion is almost negligible. The resultant misalignment between the cables and the idler pulleys is also within reasonable limits, avoiding the cables to jump out of their path. This twisting of the cables, however, limit the rotation of the instrument shaft to ±180°, at which point the cables will rub on each other, creating friction and wear.

It is important also to note that, since the most demanding force constraint is on the gripping joints, $L_6$ and $L_7$ are running in an opposite phase thru the proximal joint idler pulleys, where both coupling torques are canceled.

The references $A_1$ to $A_7$ identify the successive joint axis.

FIG. 15 shows a 3D layout of the cabling for each 7-DOF endoscopic micro-manipulator, related to the cabling schematics described before with the joints of FIG. 13.

To hold in the 3D space all the components of the cabling scheme, like idler pulleys, ball bearings, and positioning pins and screws, special parts were developed, guaranteeing the perfect positioning and support of all the joint components and allowing the routing of the different cables, considering the complex design of FIG. 15. Special attention was paid to the assembly precision of the mechanism. Since each idler tube is radial and axially positioned by six external miniature bearings (three on each extremity) as described here above with reference to FIGS. 10 and 11, their precise positioning is guaranteed by mounting them on a unique base part 50, 50', schematically illustrated in FIG. 16, whose production process, for example by CNC milling machining, ensures extremely fine tolerances. Both the proximal and distal links of a coaxial joint have a set of base parts 50, 50', which are fixed together by miniature screws, having their alignment guaranteed by positioning pins. In FIG. 16, the left side drawing shows the assembled joint as described above previously and the right side drawing shows the joint in the base parts 50, 50', in a mounted state.

As explained before, the distal link has an axial rotation movement in relation to the proximal one. Due to the lack of space, this axial rotation and the linear axial movement constraints are guaranteed by six additional miniature ball bearings 51, which are fixed to the distal set of base parts, in a configuration similar to the one used for the idler tubes, as illustrated in FIG. 17. In this way, the miniature ball bearings are in direct contact with an external proximal tube 52, which is fixed to the proximal set of base parts, enabling the precise rotation of the distal set of base parts in relation to the proximal set of parts. The top drawing of FIG. 17 Illustrates the joint of FIG. 16 in top view with a proximal link and a turning distal link, the bottom left drawing illustrates the external bearings 51 on the joint and the bottom right drawing illustrates a cut view of the joint in a tube 52.

In another aspect, the present invention relates to a mechanical system using the cable transmission described herein to form a teleoperated mechanical device as will be described in detail now.

FIG. 18 gives an overview of the endoscopic unit, with two micro manipulators, whose design details were explained previously, placed in an anthropomorphic and teleoperated configuration. Specifically, FIG. 18 illustrates the overall composition of this system which has a total of 14 degrees of freedom (excluding a possible camera system) with a master M, an insertion tube IT for insertion in the patient and a slave S, comprising the micromanipulators which used the cabled system described above.

This Surgical Platform can be divided in three major subsystems, which are designed to work together, achieving a force reflecting teleoperation. The first one is a 14 degree of freedom micro unit comprising two micro-manipulators, the mechanical slave S, with an anthropomorphic kinematics, equipped with an endoscopic camera system, providing triangulation and intuitive hand-eye coordination.

The shaft S which passes into the patient's P body incision is denominated insertion tube, IT, and not only brings the cable driven mechanical transmission from the exterior but also provides the stable fixation and movement of the slave S unit within the abdominal cavity, see FIG. 19 that illustrates the external positioning degrees of freedom on the insertion tube IT and the slave S inside the patient P.

The 3th subsystem comprises a mechanical master interface M, which is directly connected to the slave S through the fully mechanical cable driven transmission, in such a way that a surgeon's hand movements are reproduced in the slave's tip movements. In this way, the two handles of the master unit assume the same spatial orientation and relative position as the slave tips.

As compared with conventional endoscopic instruments, this mechanical manipulator improves the ergonomics for the surgeon, enabling a positioning of his/her hands in a natural orientation to each other, providing improved eye-hand coordination, intuitive manipulation, and an ergonomic posture.

Furthermore, to optimize the manipulation performances, a surgeon has only to control the movements of the instrument tips, without having the need to hold the insertion tube IT in its desired position within the abdominal cavity. Then, the insertion tube IT should be connected to an external positioning mechanism, linked to a fixed external reference (like ground, surgical bed, etc), which should provide the required 4 DOF, see FIG. 19, to fix and move the endoscopic subsystem inside the body of a patient P. To optimize force transmission and force feedback, the manipulators composing the master-slave system are designed to have light weight, low inertia, high stiffness and low friction in the joints and mechanical transmission. Finally, the endoscopic unit of the system, which enters the patient's body, is completely bio-compatible and might be able to be decoupled from the manipulators and sterilized.

In order to provide the desired mobility needed to perform complicated surgical procedures, like pulling and cutting tissue or eventually suturing, the internal DOFs are given by the two endoscopic micro-manipulators 60, 61, which exhibit high dexterity, high payload capacity, stiffness and precision inside the patient's body. In order to be as intuitive to control as possible, the degrees of freedom are designed to resemble a simplified human arm. The stereoscopic camera will be located between the two manipulators 60, 61, providing eye-manipulator alignment similar to human eye-hand alignment, and thus enhancing the telepresence and intuitiveness of the system. This aims to give the impression to the surgeon that he/she is operating inside the patient's body with his/her own two hands.

Anthropomorphic joint approximations can be modelled at varying degrees of accuracy and complexity. The level of complexity needed for a suitable representation depends highly on the desired tasks to be performed. For this specific system, since we aim to control the position and orientation of the end-effector in the 3D space, the movement of each anthropomorphic micro-manipulator 60, 61 is achieved through the articulation of six single-axis revolute joints plus the gripper.

The manipulator 60 degrees of freedom are labelled from 1 to 7, from the proximal to the distal joint, in the order shown in FIG. 20 which corresponds to FIG. 13 above and its description applies correspondingly.

The shoulder abduction-adduction and flexion-extension are then modelled as a composition of two intersecting axes, J1 and J2. The elbow flexion-extension is modelled by a single axis parallel to the second shoulder axis, J3. Forearm prono-supination takes place between the elbow and wrist joints as it does in the physiological mechanism, J4, while two orthogonal joints, J5 and J6, represent the wrist flexion-extension and radial-ulnar deviation. The offset between J5 and J6 is due to the physical limitation of having two cable actuated joints with intersecting axis. Finally, the gripper actuation is represented by J7 and is a result of the actuation of both gripper blades about the same axis. The resultant kinematics is identical to the Elbow Manipulator, which is considered to be the optimal kinematics for a general 6-DOF revolute joint manipulator.

To allow the insertion of the endoscopic micro-manipulators 60, 61 inside the abdominal cavity, they are first set to a strait position, aligned with the insertion tube IT axis, and then, after being inserted inside the patient's body, they are finally rotated to their anthropomorphic working configuration, this process being illustrated In FIG. 21.

In this way, the available cross section diameter for each arm manipulator is maximized, for the same insertion tube IT diameter, specially compared with solutions where both arm manipulators are inserted at the same time, in a parallel configuration, as shown in FIG. 22. With this configuration, the micro-manipulators diameter can be doubled and their cross section magnified 4 times, enabling a significant increasing in the achieved stiffness of the system.

FIG. 23 represents a 3D Model of the endoscopic unit 60, 61 which uses the principles of the present invention as described above with cable transmission and degrees of freedom (J1-J7, see the above description).

To reproduce the movements of surgeon's both hands to the corresponding movements at the instrument grippers a fully mechanical master-slave is used, making use of the novel cable driven transmission described before. An overview of the master-slave system is shown in FIG. 24 comprising the master M, the insertion tube IT and the slave S, this typically comprising the endoscopic unit illustrated in FIG. 23 and preceding figures, as described herein.

The system comprises two sub-teleoperated systems working in parallel. In each one of those systems, an endoscopic micro-manipulator, whose design details were explained above, is mechanically connected to another cable driven manipulator, with exactly the same transmission layout, in such a way that, when one of the systems is moved, the other one has a corresponding movement. In other words, the joint spaces of both systems are equivalent:

$$M_q = S_q, \forall M_q \in W_{M_q} \cap M_q \in W_{M_q}$$

This feature can be achieved by directly connecting both master and slave actuated pulleys for each degree of freedom, $^M M_i$ and $^S M_i$, as shown on FIG. 25 which illustrates the cabling schematics of the system. This is similar to the system described above in relation to FIG. 14 and its description applies correspondingly. Indeed, in FIG. 25, the same system is illustrated but only doubled to consider both "arms" of the manipulators 60, 61.

The cabling schematic for the entire teleoperated system is then represented in FIG. 26. It corresponds to the system of FIG. 25 which is doubled (one for the slave S and one for the master M) and the description made above in relation to preceding figures (in particular FIGS. 14 and 25) apply correspondingly here since the overall system works in an identical way.

With this teleoperated system, the ergonomics of the surgeon is visibly improved. He does not have to stand up with his hands in a non ergonomic position, does not have to manipulate long endoscopic instruments with only 4 DOFs and does not have to adapt to the mirroring effect due to the incision in the patient's body. The surgeon can sit comfortably on a chair, with supported elbows, and with his hands positioned in a natural orientation to each other. Placing the endoscopic camera between the two micromanipulators, aligned with the insertion tube, together with a properly placed of output screen, the surgeon also will be able to manipulate his own viewing direction.

In order to be placed, fixed and moved within the abdominal cavity, the teleoperated system (master M, insertion tube IT and slave S) supported by an external positioning manipulator 100 (see FIG. 27), which is fixed relatively to an operating table 101, able to provide external degrees of freedom to the endoscopic micro-manipulators, in such a way that they can be inserted, positioned and moved within the abdominal cavity of a patient.

An example of such an external positioning device 100 illustrated in FIG. 27 is given in PCT/IB2011/053576, the content of which is incorporated by reference in its entirety in the present application.

Although the present invention has been exemplified by an application on a micro-mechanism for performing minimally invasive surgical procedures, it may also be used for other forms of endoscopic surgery as well as open surgery and also in other devices, not limited to medical applications.

The present mechanical system could also be employed for any suitable remote actuated application requiring a dexterous manipulator with high stiffness and quality force feedback. It can be applied in system with different sizes and different kinds of remote actuations, from manual to computer controlled control.

Moreover, while this invention has been particularly shown and described with references to preferred embodiments thereof, it will be understood by those skilled in the art that various changes in form and details may be made therein without departing from the spirit and scope of the invention as defined by the appended claims, for example by way of equivalent means. Also the different embodiments disclosed may be combined together according to circumstances.

REFERENCES

R. Taylor, P. Jensen, L Whitcomb, A. Barnes, R. Kumar, D. Stoianovici, P. Gupta, Z. X. Wang, E. deJuan, and L. Kavoussi, "A steady-hand robotic system for microsurgical augmentation, Int. J. Robot. Res., vol. 18, No. 12, pp. 1201-1210, 1999.

M. C. Cavusoglu, F. Tendick, M. Cohn, and S. S. Sastry, "A laparoscopic telesurgical workstation," IEEE Trans. Robot. Autom., vol. 15, no. 4, pp. 728-739, August, 1999.

M. Mitsuishi, J. Arata, K. Tanaka, M. Miyamoto, T. Yoshidome, S. Iwata, S. Warisawa, and M. Hashtzume, "Development of a remote minimally invasive surgical system with operational environment transmission capability," in Proc. 2003 IEEE Inf. Conf, Robot. Autom., Taipei, Taiwan, pp. 2663-2670.

H. Mayer, I. Nagy, A. Knoll, E. U. Schirmbeck, and R. Bauemschmitt, "The Endo[PA]R system for minimally invasive robotic surgery," in Proc. 2004 IEEE/RSJ Int. Conf. Intell. Robots Syst., Sendai, Japan, pp. 3637-3642.

G. Guthart and J. Salisbury, "The intuitive telesurgery system: Overview and application," in Proc. 2000 IEEE Int. Conf. Robot. Autom., San Francisco, CA, pp. 618-621.

M. Tavakoli, R. V. Patel, and M. Moallem, "A force reflective master-slave system for minimally invasive surgery," in Proc. 2003 IEEE/RSJ Int. Conf. Intell. Robots Syst., Las Vegas, NV, pp. 3077-3082.

U. Seibold, B. Kubler, and G. Hirzinger, "Prototype of instrument for minimally invasive surgery with 6-axis force sensing capability," in Proc. 2005 IEEE Int. Conf. Robot. Autom., Barcelona, Spain, pp. 496-501.

H. Das, T. Ohm, C. Boswell, R. Steele, G. Rodriguez, S. Charles, and D, Istrata, "Dexterity-enhanced teterobotic microsurgery," in Proc. 8th Int. Conf. Adv, Robot., 1997, pp. 5-10.

G. W. Dachs and W. J. Peine, "A novel surgical robot design: Minimizing the operating envelope within the sterile field," in Proc. 28th Annu. Int. Conf. IEEE Eng. Med. Biol. Soc., New York, 2006, pp. 1505-1508.

D. J. Abbott, C. Becke, R. I. Rothstein, and W, J. Peine, "Design of an endoluminal NOTES robotic system," in Proc. 2007 IEEE/RSJ Int. Conf. Intell. Robots Syst., San Diego, CA, pp. 410-416.

K. Ikuta, K. Yamamoto, and K. Sasaki, "Development of remote microsurgery robot and new surgical procedure for deep and narrow space," in Proc. 2003 IEEE Int, Conf. Robot. Autom., Taipei, Taiwan, pp. 1103-1108.

R. Nakamura et al., "Multi-DOF forceps manipulator system for laparoscopic surgery-mechanism miniaturized & evaluation of new interface," in Proc. 4th Int. Conf. Med. Image Comput. Comput.-Assist. Interv., 2000, pp. 606-613.

H. Yamashita, A. Iimura, E. Aoki, T. Suzuki, T. Nakazawa, E. Kobayashi, M. Hashizume, I. Sakuma, and T. Dohi, "Development of endoscopic forceps manipulator using multi-slider linkage mechanisms," presented a the 1st Asian Symp. Comput.-Aided Surg.—Robot. Image-Guided Surg., Tsukuba, Japan, 2005.

J. Arata, M. Mitsuishi, S. Warisawa, and M. Hashizume, "Development of a dexterous minimally-invasive surgical system with augmented force feedback capability," in Proc. 2005 IEEE/RSJ Int. Conf. Intell. Robots Syst., pp. 3207-3212.

D. Salle, P. Bidaud, and G. Morel, "Optimal design of high dexterity modular MIS instrument for coronary artery bypass grafting," in Proc. 2004 IEEE Int. Conf. Robot. Autom., New Orleans, LA, pp. 1276-1281.

Y. Kobayashi, S. Chiyoda, K. Watabe, M. Okada, and Y. Nakamura, "Small occupancy robotic mechanisms for endoscopic surgery," in Proc. Int. Conf. Med. Comput. Comput.-Assist. Interv., 2002, pp. 75-82.

P. Dario, M. C. Carrozza, M. Marcacci, S. D'Attanasio, B. Magnami, O. Tonet, and G.Megali, "A novel mechatronic tool for computer-assisted arthroscopy," IEEE Trans. Inf. Technol. Biomed., vol. 4, No. 1, pp. 15-29, March 2000.

J. Peirs, D. Reynaerts, H. V. Brussel, G. D. Genem, and H.-W. Tang, "Design of an advanced tool guiding system for robotic surgery," in Proc. 2003 IEEE Int. Conf. Robot. Autom., Taipei, Taiwan, pp. 2651-2656.

N. Simaan, R. Taylor, and P. Flint, "A dexterous system for laryngeal surgery: Multi-backbone bending snake-like slaves for teleoperated dexterous surgical tool manipulation," in Proc. 2004 IEEE Int. Conf. Robot. Autom., New Orleans, LA, pp. 351-357.

K. Ikuta, T. Hasegawa, and S. Daifu, "Hyper redundant miniature manipulator 'hyper finger' for remoteminimally invasive surgery in deep area," in Proc. 2003 IEEE Int. Conf. Robot. Autom., Taipei, Taiwan, pp. 1098-1102.

F. Focacci, M. Piccigallo, O. Tonet, G. Megali, A. Pietrabissa, and P. Dario, "Lightweight hand-held robot for laparoscopic surgery," in Proc. 2007 IEEE Int. Conf. Robot. Autom., Rome, Italy, pp. 599-604.

C. Ishii and K. Kobayashi, "Development of a new bending mechanism and its application to robotic forceps manipulator," in Proc. 2007 IEEE Int. Conf. Robot. Autom., Rome, Italy, pp. 238-243.

What is claimed:

1. A teleoperated surgical device for performing a surgical procedure within an incision point at a patient's body, the device comprising:
a slave unit comprising a plurality of slave links interconnected by a plurality of slave joints;
an instrument shaft operatively coupled to the slave unit;
an end-effector coupled to a distal end of the instrument shaft;
a master unit comprising a plurality of master links interconnected by a plurality of master joints;
a handle coupled to the master unit for operating the teleoperated surgical device;
a transmission system configured to transmit motion, responsive to movement at the handle, from the master unit to the slave unit to cause the end-effector to move in three degrees-of-freedom and up to seven degrees-of-freedom within the patient's body,
wherein movement at the handle transmits motion from the master unit to the slave unit by actuating a first pulley to generate cable motion in a first direction and actuating a second pulley to generate cable motion in a second direction opposite to the first direction while maintaining a constant closed loop cable length to thereby move the end-effector in a degree-of-freedom within the patient's body.

2. The device of claim 1, wherein the transmission system comprises a plurality of actuators operatively coupled to the plurality of slave links such that movement at the handle transmits motion from the master unit to the slave unit via the plurality of actuators to move the end-effector within the patient's body.

3. The device of claim 1, wherein movement at the handle in a degree-of-freedom causes the transmission system to actuate the slave unit to move the end-effector in a same degree-of-freedom.

4. The device of claim 1, wherein movement at the handle transmits motion from the master unit to the slave unit via the transmission system to move the end-effector at a predetermined selected ratio relative to movement at the handle.

5. The device of claim 1, wherein input commands from an operator cause movement of the end-effector according to the input commands.

6. The device of claim 5, wherein the input commands comprise the operator moving the handle, and wherein movement of the handle corresponds to an analogous scaled increment movement of the end-effector.

7. The device of claim 1, wherein each of the slave unit and the master unit comprises two slave manipulators and two master manipulators, respectively, and wherein each of the two master manipulators are configured to be operated independently from the other.

8. The device of claim 1, wherein the transmission system is configured such that each of the plurality of slave links of the slave unit and each of the corresponding plurality of master links of the master unit move parallel to each other when operating the teleoperated surgical device.

9. The device of claim 1, wherein each of the slave unit and the master unit are configured to be locked in a stationary configuration when a surgeon is not holding the handle and when the device is in an active position.

10. The device of claim 1, further comprising an external positioning mechanism operatively coupled to a slave link of the slave unit and to a fixed external reference, the external positioning mechanism comprising a plurality of external positioning mechanism links interconnected by a plurality of external positioning mechanism joints and configured to provide, movement of the instrument shaft in up to four degrees-of-freedom about the incision point.

11. A method for remotely operating a teleoperated surgical device to perform a surgical procedure within an incision point at a patient's body, the method comprising:
selecting the teleoperated surgical device comprising a slave unit comprising a plurality of slave links interconnected by a plurality of slave joints, an instrument shaft operatively coupled to the slave unit, an end-effector coupled to a distal end of the instrument shaft, a master unit comprising a plurality of master links interconnected by a plurality of master joints, a handle coupled to the master unit for operating the teleoperated surgical device, and a transmission system configured to transmit motion from the master unit to the slave unit to cause the end-effector to move in three degrees-of-freedom and up to seven degrees-of-freedom within the patient's body;
inserting the end-effector through the incision point such that the instrument shaft passes into the patient's body at the incision point; and
moving the handle to transmit motion from the master unit to the slave unit by actuating a first pulley to generate cable motion in a first direction and actuating a second pulley to generate cable motion in a second direction opposite to the first direction while maintaining a constant closed loop cable length to thereby move the end-effector in a degree-of-freedom within the patient's body.

12. The method of claim 11, wherein moving the handle in a degree-of-freedom causes the transmission system to actuate the slave unit to move the end-effector in a same degree-of-freedom.

13. The method of claim 11, wherein moving the handle transmits motion from the master unit to the slave unit via the transmission system to move the end-effector at a predetermined selected ratio relative to movement at the handle.

14. The method of claim 11, wherein each of the slave unit and the master unit comprises two slave manipulators and two master manipulators, respectively, the method further comprising operating each of the two master manipulators independently from the other.

15. The method of claim 11, further comprising locking each of the slave unit and the master unit in a stationary configuration when a surgeon is not holding the handle and when the device is in an active position.

* * * * *